(12) United States Patent
Sundrehagen et al.

(10) Patent No.: US 7,166,473 B2
(45) Date of Patent: Jan. 23, 2007

(54) TRANSFERRIN ASSAY

(75) Inventors: Erling Sundrehagen, Oslo (NO); Asgeir Husa, Oslo (NO); Ingar Eilertsen, Oslo (NO)

(73) Assignee: Axis-Shield ASA, Oslo (NO)

( * ) Notice: Subject to any disclaimer, the term of this patent is extended or adjusted under 35 U.S.C. 154(b) by 368 days.

(21) Appl. No.: 10/167,983

(22) Filed: Jun. 10, 2002

(65) Prior Publication Data

US 2003/0087450 A1    May 8, 2003

Related U.S. Application Data

(63) Continuation of application No. PCT/GB00/04732, filed on Dec. 11, 2000.

(60) Provisional application No. 60/170,242, filed on Dec. 10, 1999.

(30) Foreign Application Priority Data

Dec. 10, 1999 (GB) .................. 9929308.6

(51) Int. Cl.
*G01N 33/00* (2006.01)

(52) U.S. Cl. .................. 436/87; 436/808; 436/811; 210/634; 210/644; 210/645

(58) Field of Classification Search .................. 436/87, 436/808, 811; 210/634, 644, 645
See application file for complete search history.

(56) References Cited

U.S. PATENT DOCUMENTS

| | | | |
|---|---|---|---|
| 4,626,355 A | * | 12/1986 | Joustra et al. .............. 210/635 |
| 5,352,616 A | * | 10/1994 | Sundrehagen .............. 436/501 |
| 5,788,845 A | | 8/1998 | Jeppsson .................. 210/635 |
| 5,798,212 A | * | 8/1998 | Sundrehagen .............. 435/7.1 |
| 6,103,478 A | * | 8/2000 | Sundrehagen .............. 435/7.1 |
| 6,716,641 B1 | * | 4/2004 | Sundrehagen .............. 436/514 |

FOREIGN PATENT DOCUMENTS

| WO | WO-96/26444 | 8/1996 |
|---|---|---|
| WO | WO-99/00672 | 1/1999 |

* cited by examiner

*Primary Examiner*—Monique T. Cole
(74) *Attorney, Agent, or Firm*—Schwegman, Lundberg, Woessner & Kluth P.A.

(57) ABSTRACT

The invention relates to an assay method for assessing a transferrin variant or combination of transferrin variants for the diagnosis and monitoring of alcoholism, and to kits for performing the assay. In particular, the invention provides a method of producing an algorithm for determining the content of a transferrin variant or combination of transferrin variants, preferably a CDT variant or combination of CDT variants, in a sample of body fluid, said method comprising: (a) obtaining at least two solutions each having known contents of asialo- (A1, A2, A3, etc.) and disialo-transferrins (D1, D2, D3, etc.); (b) determining the content in each of said solutions of a transferrin variant or combination of transferrin variants fractions substantially free from tri- and higher sialylated transferring; (c) determining the total transferrin variant content (T1, T2, T2, etc.) of said fractions; and (d) producing an algorithm capable of determining the content of any transferrin variant or combination of transferrin variants, preferably a CDT variant or combination of CDT variants, in any given sample of body fluid subjected to said determination step b).

34 Claims, 13 Drawing Sheets

| $r^2$ | 0.9153 |

TRANSFERRIN ASSAY

RELATED APPLICATIONS

This application is a continuation under 35 U.S.C. 111(a) of International Application No. PCT/GB00/04732 filed Dec. 11, 2000 and published in English as WO 01/42795 A2 on Jun. 14, 2001, which claims priority under 35 U.S.C. 119 from United Kingdom Application No. 9929308.6 filed Dec. 10, 1999, and U.S. Provisional Application No. 60/170,242 filed Dec. 10, 1999, which applications are incorporated herein by reference.

This invention relates to an assay method for assessing a transferrin variant or combination of transferrin variants for the diagnosis and monitoring of alcoholism, and to kits for performing the assay. In particular, the invention relates to an assay method for assessing a carbohydrate-deficient transferrin variant or any combination of such variants.

Serum transferrin is a glycoprotein with a molecular weight of about 80 kD which comprises a single polypeptide chain with two N-linked polysaccharide chains. These polysaccharide chains are branched and each chain may terminate in either two or three antennae, each with terminal sialic acid residues.

Wong and Regoeczi, in Int. J. Peptide Res. (1977) 9:241–248, reported that human transferrin was naturally heterogeneous, occurring in variant forms with different levels of sialylation. Such variants are generally believed to be the hexasialo, pentasialo, tetrasialo, trisialo, disialo, monosialo and asialo transferrins. Recently, it has been reported that the levels of monosialotransferrin are very low (see Landberg et al. (1995) Biochem. Biophys. Res. Comm. 210(2):267–274 and Jochen et al. Biochemica et Biophysica Acta (1998) 1380:93–101).

The asialo, monosialo and disialo variants are referred to herein as carbohydrate-deficient transferrin or CDT. The asialo variant, now known to be completely devoid of carbohydrate chains, is referred to herein as carbohydrate free transferrin or CFT.

In the normal healthy individual, the tetrasialo variant appears to predominate; however it has been reported that the asialo, monosialo, disialo and, to some degree the trisialo variants occur in elevated levels in the blood of alcoholics (see van Eijk et al. (1983) Clin. Chim. Acta 132:167–171, Stibler (1991) Clin. Chim. 37:2029–2037 and Stibler et al. in "Carbohydrate-deficient transferrin (CDT) in serum as a marker of high alcohol consumption", Advances in the Biosciences, (Ed Nordmann et al), Pergamon, 1988, Vol. 71, pages 353–357).

CDT has been shown to be an effective marker for alcohol consumption, in particular for detecting and monitoring chronic alcohol consumption, and unlike conventional tests (e.g. quantitation of γ-glutamyltransferase or measurement of mean corpuscular volume) can be used to screen for heavy alcohol intake in patients with liver disease.

Recognition of the fact that the CDT profile of alcohol abusers differs from that of abstainers or normal users, combined with the identification of the relative amounts of each CDT isoform, e.g. on the basis of the differences in the isoelectric point (pI) or charge of the different transferrin molecules, has led to the development of several diagnostic assays for CDT. These are described in the patent and scientific literature, for example in U.S. Pat. No. 4,626,355, WO 91/19983, WO 96/26444, Heil et al. (1994) Anaesthetist 43:447–453, and Dumon et al. (1996) Clin. Biochem. 29(6): 549–553).

More recent studies (for example by Landberg et al. (1995) Biochem. Biophys. Res. Comm. 210(2): 267–274), have shown, by releasing the N-glycans from each isoform of transferrin and analysing them by high-pH anion exchange chromatography, that the existence of disialo and asialo-transferrins correlates with the loss of one or both of the entire carbohydrate chains respectively from the transferrin polypeptide. This is confirmed by Jochen et al. in Biochemica et Biophysica Acta (1998) 1380:93–101.

Based on the discovery that the presence of transferrin isoforms which are completely devoid of carbohydrate (hereinafter referred to as carbohydrate free transferrin or CFT) is a strong indicator of alcoholism in the absence of any knowledge of the prevalence of any other CDT variants (i.e. monosialo, disialo or trisialotransferrin variants), the Applicants developed and described in WO 99/00672 an assay for the determination of CFT as a means of assessing alcoholism. The assay is robust, simple and quick to perform, and readily amenable to automation or compatible with existing routine clinical diagnostic laboratory procedures. This is achieved by separating the carbohydrate-containing transferrins from a sample by contacting the sample with a carbohydrate-binding ligand, e.g. a lectin, and detecting and measuring the carbohydrate-free transferrin contained in the separated, non-binding fraction.

The accuracy and thus the clinical value of each of the assay procedures mentioned above is dependent on an efficient method of separation of the individual transferrin isoforms or combination of such isoforms. As a result, relatively complex, expensive separation procedures are necessary to obtain an accurate diagnosis.

In particular, the pI or charge based methods of the prior art are primarily centred on procedures involving ion exchange chromatography. The difference in pI between the different transferrin variants is very narrow, down to $\frac{1}{10}$ of a pH unit and therefore to effect separation of CDT variants, a very good separation is required. In the case of ion exchange chromatography, this constraint effectively means that a column format must be used; batch filtration-based ion exchange procedures do not provide a sufficient separation or resolution. Column formats are however less preferred in clinical chemistry or diagnostic procedures, due to their time consuming and labour intensive operation, problems of storage and transport, incompatibility with commonly-used systems etc.

Due to the low levels of CFT generally found in serum samples (even in alcoholics only about 1% of the transferrin molecules are asialotransferrin or CFT), an efficient separation is similarly required to effect separation of CFT from any carbohydrate containing transferring in the assay described in WO 99/00672.

There is therefore a need for an alternative assay method in which incomplete or partial separation of transferrin variants, e.g. one or more CDT variants, can be tolerated without affecting the clinical value of the assay. The present invention seeks to address this need.

Mårtensson et al. (Alcoholism: Clin. and Exp. Research (1997) 21(9):1710–1715) describe a clinical study of transferrin variant concentrations by means of ion exchange HPLC in combination with RIA analysis of the transferrin content of the HPLC fractions eluted. Higher clinical sensitivity was found for measurement of disialotransferrin alone and with the sum of asialo-, monosialo- and disialo-transferrins compared to asialo- and monosialo-transferrins alone. A much lower clinical sensitivity was found with trisialotransferrins. Mårtensson et al. focus on the differences in clinical signals between the different transferrin variants with a view to selecting the best transferrin variant or combination of variants. No correlation figures for the different variants are reported.

In June 1999, Professor Jan-Olof Jeppson working at the University of Malmo, Sweden reported a weak correlation (correlation coefficient $R^2=0.63$) between asialo and disialo-transferrins using the procedure of ion exchange chromatography and spectrophotometric detection at 470 nm as described in WO 95/04932.

Contrary to the findings of Jeppson, we have now surprisingly found a high level of correlation between the asialo- and disialo-transferrin contents of serum samples. This has led to the development of an improved assay procedure for determining the content of any desired transferrin variant or combination of transferrin variants, in particular asialo- or disialo-transferrin or CDT, in a body fluid sample in which a less efficient separation of transferrin variants can be tolerated. This allows much simpler separation methods to be used for the assessment of alcohol consumption.

Thus, according to one aspect, the present invention provides a method of producing an algorithm for determining the content of a transferrin variant or combination of transferrin variants, preferably a CDT variant or combination of CDT variants, in a sample of body fluid, said method comprising:
(a) obtaining at least two solutions each having known contents of asialo- (A1, A2, A3, etc.) and disialo-transferrins (D1, D2, D3, etc.);
(b) subjecting each of said solutions to a separation method whereby to separate fractions substantially free from tri- and higher sialylated transferrins
(c) determining the total transferrin variant content (T1, T2, T3, etc.) of said fractions; and
(d) producing an algorithm capable of determining the content of any transferrin variant or combination of transferrin variants, preferably a CDT variant or combination of CDT variants, in any given sample of body fluid subjected to said separation method.

As mentioned further below, however, the purpose of the separation step used in the methods herein described is essentially to remove all or substantially all tri-, tetra-, penta- and hexa-sialotransferrins (non-target variants) from the sample, allowing the remaining target variants (asialo-, monosialo- and disialotransferrins) to be determined Thus viewed from a broader aspect, the invention provides a method of producing an algorithm for determining the content of a transferrin variant or combination of transferrin variants, preferably a CDT variant or combination of CDT variants, in a sample of body fluid, said method comprising:
(a) obtaining at least two solutions each having known contents of asialo- (A1, A2, A3, etc.) and disialo-transferrins (D1, D2, D3, etc.);
(b) determining the content in each of said solutions of a transferrin variant or combination of transferrin variants in fractions substantially free from tri- and higher sialylated transferring;
(c) determining the total transferrin variant content (T1, T2, T3, etc.) of said fractions; and
(d) producing an algorithm capable of determining the content of any transferrin variant or combination of transferrin variants, preferably a CDT variant or combination of CDT variants, in any given sample of body fluid subjected to said determination step b).

In general, the algorithm produced in accordance with the invention will be one capable of determining the actual content or amount of asialo- or disialo-transferrin, or the actual content or amount of asialo-, monosialo- and disialo-transferrins (i.e. CDT) in any sample of body fluid.

As will be apparent, the algorithm will be specific to a given determination step or separation method carried out under specific conditions. Preferably, the algorithm for use in the invention will be based upon a quantitation of each of the isoforms of transferrin having zero, one or two sialic acid residues per molecule. Most preferably, the algorithm may be produced on the basis of the high correlation between the content of asialo- (CFT) and disialo-transferrins in a sample, preferably also the low level of monosialotransferrin.

Based on the correlation determined between asialo- and disialotransferrins, the invention essentially provides a method of producing a calibration curve specific to any given determination step or separation method and which may be used to calculate the content or amount of any transferrin variant or variants in any given sample of body fluid. The correlation coefficient between asialo- and disialotransferrin may be determined using mathematical techniques and correlations standard in the art, e.g. least squares analysis.

More specifically, the algorithm produced in accordance with the invention may be defined by at least one of the following equations:

$$A=(T-d.b)/(c+d.a)$$

$$D=b+a(T-d.b)/(c+d.a)$$

$$CDT=A+D=b+(a+1)(T-d.b)/(c+d.a)$$

(wherein

T represents the determined total transferrin content in the determined fraction (or in the separated fraction following separation);

A represents the actual asialotransferrin content in the sample;

D represents the actual disialotransferrin content in the sample;

CDT represents the actual total content of asialo-, monosialo- and disialotransferrins in the sample;

a and b are constants defining the correlation between A and D in any serum sample; and c and d are constants specific to the determination step or separation method).

In a further aspect the invention provides a method for determining the content of a transferrin variant or combination of transferrin variants, preferably a CDT variant or combination of CDT variants, in a body fluid for use in the assessment of alcohol consumption, said method comprising:
(a) subjecting a sample of said body fluid to a separation method capable of separating a fraction substantially free from tri- and higher sialylated transferrins;
(b) determining the total transferrin variant content in said fraction; and
(c) determining the content of any transferrin variant or combination of transferrin variants, preferably the content of any CDT variant or combination of CDT variants, in said sample using an algorithm obtained in accordance with a method as herein described.

However, the separation step need not be provided if an alternative way to determine the target variants (asialo-, monosialo- and disialo-transferrins) is available. Furthermore, it is also possible to determine the content of only a portion of the target variants, so long as the portion of target variants is constant and reproducible.

Thus viewed from a broader aspect, the invention provides a method for determining the content of a transferrin variant or combination of transferrin variants, preferably a CDT variant or combination of CDT variants, in a body fluid for use in the assessment of alcohol consumption, said method comprising:

(a) determining the content in a sample of said body fluid of a transferrin variant or combination of transferrin variants in a fraction substantially free from tri- and higher sialylated transferrins;

(b) determining the total transferrin variant content in said fraction; and (c) determining the content of any transferrin variant or combination of transferrin variants, preferably the content of any CDT variant or combination of CDT variants, in said sample using an algorithm obtained in accordance with a method as herein described.

In the assay in accordance with the invention, the measured transferrin variant content can be used to determine the actual levels of any transferrin variant or variants in the sample on the basis of a calibration derived from the correlation discovered for the levels of asialo- and disialotransferrins.

As will be generally understood, the determination step or separation method used in performing the assay in accordance with the invention will be the same as that used to produce the algorithm or calibration curve, such determination steps or separation methods being performed under the same set of conditions.

As used herein, the terms "determining" or "assessing" include both quantitation in the sense of obtaining an absolute value for the amount or concentration of transferrin variant(s) in the sample, and also semi-quantitative and qualitative assessments or determinations. An index, ratio, percentage or similar indication of the level or amount of transferrin variant(s), for example relative to total transferrin (i.e. all transferrin variants) may be obtained.

The assay method of the invention provides a convenient method for the determination of alcohol consumption by assaying the level of a transferrin variant or combination of transferrin variants in a body fluid, preferably a blood-derived body fluid, and may particularly find utility in the diagnosis and monitoring of alcoholism or alcohol abuse. Both asialo- and disialotransferrins, as well as a combination of asialo-, monosialo- and disialotransferrins have previously been shown to be a good indicator or marker for alcoholism or alcohol abuse, and by assaying the content of any of these in samples of body fluid, a distinction may be found between alcoholics and alcohol abusers and non-alcohol abusers or social drinkers.

The body fluid used in the assay method of the invention may be any transferrin-containing body fluid for example, synovial fluid, amniotic fluid or cerebrospinal fluid, but will generally be blood or a blood derived sample. When this is the case, the sample used for analysis will preferably be cell-free and hence, either serum or plasma may be used. The sample may be treated prior to being used in the assay method of the invention, for example, it may be diluted by adding a buffer or other aqueous medium.

The purpose of the separation step used in the methods herein described is essentially to remove all or substantially all tri-, tetra-, penta- and hexasialotransferrins (non-target variants) from the sample, allowing the remaining target variants (asialo-, monosialo- and disialotransferrins) to be determined.

Where a determination step is referred to in relation to the methods herein described, this may in a preferred embodiment be a separation step. However, it may also be desirable in some circumstances to directly determine the content of the target variant(s) in a fraction of the sample without physically separating the fractions out.

For example, various immunoassay techniques are available which could allow detection or quantitation of target transferrin variant(s) in a body fluid. The antibody described in EP 0 605 627 is specific for a transferrin homolog found in alcoholics, or CDT, and therefore such an antibody may be used to determine the content of a target transferrin variant, or combination of transferrin variants. Provided that the antibody binds a constant fraction of the sample which is substantially free from tri- and higher sialylated transferrin it is possible to produce an algorithm in accordance with the invention.

Thus, in a particularly preferred aspect of the invention, the determination step is effectively a direct determination or direct measurement of the content of the target transferrin variants, or a combination of said target variants.

Transferrin preparations which may be regarded as substantially free from tri-, tetra-, penta- and hexasialotransferrins are those comprising less than 20%, more preferably less than 10%, e.g. less than 5% transferrin variants having three or more sialic acid residues per molecule.

Provided that the determination step or separation method is reproducible, separation of all asialo-, monosialo- and disialotransferrins or determination of the content of each is not required when carrying out the invention. Although possible to isolate all CDT variants, clinically valuable results can be obtained by separating or determining only a fraction of these variants. What matters is that the separated or determined fraction of each variant is reproducible (i.e. essentially constant) for a given determination step under given conditions, or for a given separation method and given separation conditions. Quantitation (in the sense of obtaining an absolute value) of any or all of the CDT variants is not essential in carrying out the methods herein described.

Following separation (where separation is carried out), or in the case of a determination step, the fraction containing the desired target variants will typically comprise at least 60t, preferably at least 70 to 80%, e.g. 90 to 95% of the asialo- and monosialo-transferrin variants present in the sample prior to separation or determination. The disialotransferrin content of the separated or determined fraction will generally be at least 20%, preferably up to 60 to 70%, particularly preferably 20 to 50%, e.g. about 30% of the total disialotransferrin content of the sample prior to separation or determination.

In the separated or determined fraction containing the desired target variants, at least 40%, preferably at least 60%, e.g. at least 70 to 80% of the transferrin molecules will carry a carbohydrate chain or a residue thereof. The separated or determined fraction will typically comprise less than 20%, e.g. 10 to 15% asialotransferrin (or CFT), less than 5% monosialotransferrin and 70 to 80%, e.g. about 75% disialotransferrin. An amount of trisialotransferrin, typically up to 20%, preferably up to 10%, e.g. up to 5%, can be tolerated without affecting the clinical value of the assay.

Thus for example the fraction to be determined or separated could consist essentially of asialotransferrin or it could could consist essentially of disialotransferrin, but in either case some or all of monosialotransferrin (and/or trisialotransferrin) could be present in the same fraction. Because the amount of monosialo (or trisialo-) transferrin is low relative to the amounts of asialo- and disialo-transferrin, this will not interfere significantly with the results of an assay in accordance with the invention.

Conveniently, ion exchange chromatography may be used to remove all or substantially all of the tri- and higher sialylated transferrins in any of the methods herein described. Ion exchange as a means of separating the various isotransferrin components is well known, and is described for example in U.S. Pat. No. 4,626,355, Heil et al. (supra) and WO 96/26444. Advantageously, an anion exchange chromatography step may be used, with the chromatography conditions (e.g. pH and ion binding strength) selected to permit retention of the desired transferrin variants (e.g. hexa-, penta-, tetra- and tri-sialo transferrin, and optionally some or all of the disialo fraction).

Appropriate conditions e.g. buffering-capacity of the resin, sample/equilibration/elution buffer pH and/or ionic strength can readily be determined according to techniques known in the art, and according to the separation desired to be achieved. As is known in the art, prior to ion exchange, the sample may be treated with iron-containing buffer to saturate the iron-binding sites in the transferrin molecules in the sample.

Conveniently, according to techniques known in the art, chloride may be used as the counterion in the ion exchange procedure in order to achieve the desired separation. Thus, appropriate amounts of chloride ion present in the chromatography procedure necessary to achieve retention of the desired transferrin variants may be determined by routine experiments, and may depend on the precise conditions, batch of chromatography medium etc. The procedure can be monitored by isoelectric focusing or HPLC analysis, again according to standard techniques known in the art.

The ion exchange chromatography step may be carried out in any convenient manner known in the art according to choice, e.g. in a batch or column format. Likewise, the conditions may be selected to achieve the separation (i.e. depletion or removal) in any desired manner, for example by retaining the isotransferrin variants it is desired to remove (i.e. target variants), or by pre-treating the sample by ion exchange such that the "undesired" (i.e. non-target) variants do not absorb to the medium, and the remainder of the sample is separated and then eluted from the ion exchange medium. Advantageously, the chromatography conditions are set to permit retention of the "undesired" transferrin variants.

As exemplary of ion exchange conditions which may be used, mention may be made of Whatman QASL anion exchange resin buffered at pH 6.3, which may be used to bind the trisialo and higher sialylated transferrins.

Alternatively, separation of target and non-target variants may be achieved using a binding ligand capable of binding selectively either to the target or non-target transferrin variants. Any binding ligand which has an affinity for the target or non-target transferrin variants may thus be used to separate the target variants from other transferrin variants in the sample. Preferably, the binding ligand may be a carbohydrate-binding ligand such as a lectin or mixture of lectins, e.g. as described in WO 99/00672. As noted in this earlier patent, 100% separation of CFT cannot always be achieved in practice. It has now been found that transferrin variants having a low carbohydrate content, in particular monosialo- and disialo-transferrins, bind with a low affinity to carbohydrate-binding ligands, such as lectins. In particular, it has been found that such variants bind to carbohydrate-binding ligands with a lower affinity than the transferrin variants having a higher or high carbohydrate content (i.e. the higher sialylated transferrins, e.g. tri-, tetra- and pentasialotransferrins). Separation methods using carbohydrate-binding ligands, for example lectins, are thus effective to remove higher sialylated transferring (e.g. tri-, tetra-, penta- and hexa-sialotransferrins), but are generally less effective in removing lower sialylated transferring (e.g. mono- and di-sialotransferrins). The result is an incomplete separation of CFT in which the separated "non-binding" fraction will typically contain some or all of the mono- and disialotransferrins in addition to asialotransferrin (CFT). As noted previously, the assay method in accordance with the invention can tolerate incomplete separation of transferrin variants without compromising the clinical value of the assay.

When the body fluid comprising transferrin variants is contacted with the carbohydrate-binding ligands, substantially all of the higher sialylated variants (tri-, tetra-, penta- and hexa-sialotransferrins) with carbohydrate side chains or remnants thereof are retained by the carbohydrate-binding ligands. The unbound fraction containing CFT, mono- and disialotransferrins may then be separated from the other variants and collected by any suitable means.

In a particularly preferred embodiment of the invention the separation method comprises the steps of contacting a sample of body fluid with a carbohydrate-binding ligand, e.g. a lectin or mixture of lectins, followed by separation of a fraction not binding to said ligand. The total amount of transferrin in the non-binding fraction may be determined directly by measuring the transferrin not bound by the carbohydrate binding ligand. Alternatively it may be determined indirectly by determining the amount of transferrin bound to the carbohydrate binding ligand and subtracting this from the total amount of transferrin present in the sample. Generally, the direct approach is preferred.

Any carbohydrate-binding ligand or any combination thereof may be used to separate the target variants from other transferrin variants. This includes any ligand capable of binding to any carbohydrate or oligosaccharide or sugar structures. One or more carbohydrate-binding ligands may be used in the method of the invention. Where more than one ligand is being used, these may be used together or they may be used individually, for example, sequentially. The functional requirement of the carbohydrate binding ligand(s), rendering them suitable for use in the assay method of the present invention, is that they be capable of separating CDT from other transferrin variants.

Generally, the carbohydrate-binding ligand will be a protein, and very many such carbohydrate-binding proteins are known in the art and are widely described in the literature. The carbohydrate-binding protein may, for example, be an antibody, either polyclonal or monoclonal, or may be an antibody fragment for example F(ab), F(ab')$_2$ or F(v) fragments. The antibodies or antibody fragments may be monovalent or divalent and they may be produced by hybridoma technology or be of synthetic origin, via recombinant DNA technology or chemical synthesis. Single chain antibodies could for example be used. The antibody may be directed or raised against any of the carbohydrate components or structures making up the carbohydrate chains of glycosylated transferrin variants. Thus, for example, an antibody reactive with or selective for sialic acid residues might be used. Such an antibody is used in the Sialic Acid Deficient Enzyme Immunoassay (SDT-EIA) available from Medichem, Stuttgart, Germany and described in WO 97/19355.

More preferably, the carbohydrate-binding protein may be a lectin, used singularly or in combination with other lectins or with other types of carbohydrate-binding proteins, for example, antibodies. Any lectin known in the art may be used in the assay method of the invention and it may be of plant, animal, microbiological or any other origin. The literature is replete with references to different lectins which might be used, and many may be obtained commercially, for example, from Sigma.

Thus, included within the general term "lectin" as used herein, in addition to the classical plant lectins such as Concanavalin A (Con A), are carbohydrate binding proteins from microorganisms (for example, viral haemagglutinins) and higher organisms, including for example, invertebrates and mammals. Such mammalian carbohydrate binding proteins include selecting and other mammalian lectins or cell adhesion molecules (see for example Varki (1992) Current Opinion in Cell Biology 4:257–266).

Examples of suitable lectins are RCA-I (*Ricinus communis agglutinin*) which binds terminal galactose (Kornfeld et al. (1981) J. Biol. Chem. 256:6633) or Con-A (Concanavalin A), which is known to bind asparagine-linked oligosaccharides high in mannose. Other possibilities are *Crotalaria juncea* lectin which binds galactose residues (Ersson (1977) Biochim. Biophys. Acta 494:51–60), Wheatgerm agglutinin or *Limulus polyphenus* lectin which bind sialic acid (Mandal and Mandal (1990) Experientia 46:433–441) or *Sambucus nigra agglutinin* L which binds Neu5Ac/($\propto$2–6)Gal/GalNAc (Shibuya et al. (1987) J. Biol. Chem. 262:1596). As an example of a lectin derived from a micro-organism, a sialic acid specific lectin has recently been purified from the gut dwelling organism *Helicobacter pylori* (Lelwala-Guruge et al. (1993) APMIS 101:695–702).

Lectins of varying selectivity and specificity are known. Whereas some lectins may bind to a single sugar residue in a particular location on an oligosaccharide chain, for example RCA-I (from *Ricinus communis*) binds only to terminal galactose residues, some may bind to complex oligosaccharide determinants for example *Sambucus nigra* L which binds NeuSAc/($\propto$2–6)Gal/GalNAc. All are within the scope of the present invention.

Sialic acid binding lectins and other proteins represent a class of carbohydrate binding proteins of particular utility in the present invention (see the following, for example, for lists of suitable lectins and their sources: Mandal and Mandal (1990) Experientia 46:433–441); Zeng (1992) Z. Naturforsch, 47c:641–653 and Reuter and Schauer in Methods in Enzymology, Vol. 230, Chapter 10 at pages 196–198).

Particular mention may be made in this regard of *Sambucus nigra* L. Lectin, *Sambucus sielbodiana* lectin wheatgerm agglutinin, *Maackia amurensis* lectin, and *E. coli* K99 lectin. *S. nigra* L. lectin is particularly effective when used on its own, although it may equally effectively be used in combination with other lectins eg. ConA.

Some particular combinations of carbohydrate binding ligands useful for performance of the present invention are lectins from *Helicobacter pylori* and *Ricinus communis*; lectins from *Ricinus communis* and *Sambuccus nigra*; lectins from *Crotalaria junctae* and *Sambuccus nigra*; lectins from *Crotalaria junctae* and *Helicobacter pylori* and lectins from *Ricinus communis* and anti-sialic acid antibodies. The most preferred of the combinations are those which incorporate galactose-binding and sialic acid-binding ligands.

Following the binding step(s) a fraction may conveniently be collected which does not bind and which contains the CDT. Collection may be by any suitable means, for example, precipitation, centrifugation, filtration, chromatographic methods etc. Where different carbohydrate-binding ligands are used individually, different separation/collection formats may be used for each individual binding step.

Precipitation of carbohydrate-containing moieties in the sample may be achieved using lectins having known "precipitation" properties i.e. lectins capable of inducing precipitation of the moieties to which they bind. Combinations of lectins may advantageously be used for such a precipitation procedure, since differing lectin specificities increase the number of available binding sites. The non-binding (CDT) fraction may then readily be collected, for example by centrifugation or filtration to separate the precipitate.

In alternative embodiments, the carbohydrate binding ligand(s) may conveniently be immobilised to facilitate the separation and collection of the non-binding fraction. It is well known in the art to immobilise carbohydrate-binding ligands such as lectins for separation purposes, for example, in chromatographic columns, and any lectin affinity chromatography method known in the art could for example be used (see for example, Cummings (1994) Methods in Enzymology 230:66–86).

The carbohydrate-binding ligands may be immobilised by binding or coupling to any of the well known solid supports or matrices which are currently widely used or proposed for immobilisation or separation etc. These may take the form of particles, sheets, gels, filters, membranes, fibres or capillaries or microtitre strips, tubes or plates or wells etc and conveniently may be made of glass, silica, latex or a polymeric material. Techniques for binding the ligand to the solid support are also extremely well known and widely described in the literature. For example, the carbohydrate-binding ligands used may conveniently be coupled covalently to CNBr-activated Sepharose or N-hydroxysuccinimide-activated supports, optionally in the presence of low molecular weight haptens to protect the carbohydrate binding sites on the ligand. Other coupling methods for proteins are also well known in the art.

Batch separations using immobilised carbohydrate-binding ligands may be performed using a range of different formats which are known in the art.

In a different embodiment, although this is less preferred, the immobilised carbohydrate-binding ligands may be packed or arranged into a column. The body fluid comprising transferrin may be applied to the column and the transferrin variants therein contacted with the carbohydrate-binding ligands. The unbound fraction comprising CDT is separated from the bound fraction and collected.

The shape and geometry of such a column may vary depending upon the carbohydrate-binding ligands used. For example, if lectins are used as the carbohydrate-binding ligands, at low lectin concentrations a long, thin column of immobilized lectins is preferred. At high lectin concentrations, column geometry is less crucial.

Columns may be constructed using any method known in the art. If lectins are to be used as the carbohydrate-binding ligands, the columns may be constructed in either glass tubes or preferably in disposable plastic pipettes of any desired capacity. Smaller volumes may however be preferred due to economic considerations. Columns are preferably stored at around 4° C. prior to use.

The column may be flushed through with an eluant to allow or facilitate collection of the unbound fraction, in which case the eluant should preferably be administered using a calibrated micropipette to ensure the correct volume is administered. The volume administered is preferably within 3% of the desired (i.e. calibration) volume, more preferably, within 1 or 2%. Since the rate of binding to oligosaccharides is comparatively slow, especially with plant lectins, it is preferable that slow flow rates are employed to maximise lectin/carbohydrate interactions. The eluant will generally be at a temperature within 5° C. of the desired (calibration) value, e.g. 25° C., and more preferably within 1° C.

When using combinations of carbohydrate-binding ligands in a column format, either sequential columns using different ligands may be used or different ligands may be used in the same column material, either as a mixture or in a column comprising different layers, each layer having a different ligand.

In an alternative embodiment, the carbohydrate-binding ligand may be immobilised on a particulate solid phase, for example, latex, silica or polymer beads. To aid manipulation and separation, magnetic beads may be used. The term "magnetic" as used herein means that the support is capable of having a magnetic moment imparted to it when placed in a magnetic field. In other words, a support comprising magnetic particles may readily be removed by magnetic aggregation, which provides a quick, simple and efficient way of separating the fractions following the carbohydrate binding step.

Thus, the magnetic particles with non-target variant moieties attached may be removed onto a suitable surface by application of a magnetic field, for example, using a permanent magnet. It is usually sufficient to apply a magnet to the side of the vessel containing the sample mixture to aggregate the particles to the wall of the vessel and to collect the remainder of the sample, which will comprise the "non-binding, CDT-containing fraction" which may be returned for subsequent analysis.

Especially preferred are superparamagnetic particles, which include for example those described by Sintef in EP-A-106873, as magnetic aggregation and clumping of the particles during the reaction can be avoided. Magnetic particles are commercially available from a number of sources, including for example, Advanced Magnetics Inc., (USA), Amersham (UK), Bang Particles (USA), and Dynal AS (Oslo, Norway).

Functionalised coated particles for use in the present invention may be prepared by modification of the beads, for example according to U.S. Pat. Nos. 4,336,173, 4,459,378 and 4,654,267. Thus, beads, or other supports, may be prepared having different types of functionalised surface, for attachment of a desired carbohydrate-binding ligand.

Separations based on centrifugation and/or filtration are convenient. In a preferred embodiment a centrifuge tube (e.g. Eppendorf tube) and "filter cup" format may be used, and such formats are readily commercially available, for example from Millepore. Thus the sample and carbohydrate-binding ligand may be added to the cup in the tube and allowed to bind. The tube (and cup) is then spun, and the non-binding supernatant collects in the tube. The carbohydrate-binding ligand may be such as to induce precipitation of the bound carbohydrate moieties or it may be immobilised, for example as a slurry e.g. a gel or on particles. In either case, the bound carbohydrate binding fraction is retained in the cup.

As a variation of such a "tube and cup" arrangement, the cup may be provided with one or more "discs" or filters which carry immobilised carbohydrate-binding ligands.

Following the determination step or the separation step, the total content of transferrin in the separated fraction is determined. This may be done by any standard procedure known in the art for assay of transferrin, for example, by any standard immunoassay technique, e.g. an ELISA or radio-immunoassay technique. Methods for determining transferrins are described for example in U.S. Pat. No. 4,626,355 (Joustra).

An example of an ELISA method could include a sandwich assay in which an immobilised antibody specific for transferrin variants which are substantially free from tri- and higher sialylated transferrins is contacted with the sample, and then enzyme-labelled anti-transferrin antibodies (available from Dako AS, Denmark) are used to detect the bound transferrin. A preferred such immobilised antibody is the antibody described in EP 0 605 627 and in such a case it will be appreciated that the separated fraction will be the fraction of antibody-bound transferrin and that the enzyme signal will be proportional to the total transferrin content of that fraction, allowing the total transferrin to be determined in that fraction.

Many commercial assays for transferrin are available and have been described in the literature. For example an RID (radio immuno diffusion) assay based on the method of Mancini is available from Hoechst (see Mancini et al. Immunochemistry, 2:235–254 (1965)). A rocket immuno electrophoresis method is described by Laurell in Scand. J. Clin. Lab. Invest. 29 (Suppl. 124): 21–37 (1972). Particular mention may also be made of the p-article-based immunoassay method of Muller et al. in Lab. Med. 15:278 (1991). This is a very sensitive technique, based on an enhanced turbidometric method which uses a turbidometric signal but is more sensitive than traditional turbidometric methods.

For either turbidimetric or nephelometric transferrin determination, opacity will generally be generated by contacting the separated fraction or an aliquot thereof with an anti-transferrin antibody or antibody fragment, e.g. a rabbit anti-human transferrin antibody such as is commercially available from Dako of Copenhagen, Denmark. The Dako antibodies are specific to transferrin and show no cross reactions with other blood proteins that may be present in the eluate. The quantity of antibody used should of course be optimised against transferrin containing standard samples as opacification arises from the hook effect whereby multiple transferrin binding generates the opacification centres.

In the case of the "tube and cup" embodiment described above for example, the anti-transferrin antibodies may simply be added to the tube after centrifugation.

As in routine turbidimetric and nephelometric assays, a polymeric opacification enhancer, such as polyethyleneglycol, is preferably also added to the eluate.

In determining transferrin content using such measuring techniques, a kinetic reading mode may of course be used.

Before the nephelometric or turbidimetric determination is made, the fraction, antibody and enhancer may be incubated for a short period, e.g. 5 minutes to an hour for end-point measurements, preferably about 10 minutes.

The light used in the determination of opacification should have an appropriate wavelength. In this regard we have found that use of a 405 nm filter, or more preferably a 340 nm filter, yields particularly good results.

Where a separation method is to be avoided and a direct determination step is instead to be used, a suitable method is to take advantage of a proximity interaction technique. Most preferably, in this embodiment of the invention, a specific binding partner for the target transferrin variants is utilised in a proximity assay to obtain a direct determination of the amount of the target variants (asialo-, monosialo- and disialotransferrins) in the fraction(s) to be determined. An example of a suitable specific binding partner is the anti-transferrin antibody which reacts selectively with transferrin homologs found in alcoholics but not in non-alcoholics, as disclosed in EP 0 605 627.

Another means of producing a suitable specific binding partner with appropriate specificity for the target transferrin variants to be determined is to raise an antibody against a peptide immunogen which mimicks the N-glycan binding site on the transferrin molecule, for example if the peptide sequence corresponds to the amino acid sequence of human transferrin. The amino acid sequence of human transferrin is known and is published for example in Yang et al., Proc. Natl. Acad. Sci. 81: 2752–2756 (1984) or accession number PO 2787 Swiss Prot database.

Examples of suitable techniques which allow for detection of a signal due to proximity interaction between molecules are described in the literature. Such techniques include fluorescence polarisation immunoassay technology (FPIA), fluorescence quenching techniques, proximity scintillation assays and EMIT technology.

FPIA techniques are described for example in Dandliker et al., Immunochemistry 7: 799–828, (1970), and in Wei et al., Anal. Chem. 65: 3372–3377 (1993)).

Fluorescence quenching techniques are described for example in U.S. Pat. No. 3,996,345 of Ullmann et al., in which one binding partner carries a fluorescent residue and the other carries a quencher.

Proximity scintillation assays are described for example in U.S. Pat. No. 4,568,649 and EP 0 154 734 of Bertoglio-Matte. In these assays, one of the binding partners emits a short-range energy-rich radioactive signal, typically emitting β-rays, and when proximity interaction with the other binding partner occurs, a fluorophore linked to the second binding partner is excited by the radioactive energy and a fluorescent signal is generated.

A further, more complex type of fluorescent proximity assay was described in U.S. Pat. No. 5,763,189 of Buechler et al. which is based upon the measurement of Stokes shift (difference in wavelength of light which is emitted as compared to the excitation wavelength).

The EMIT technology is described for example in U.S. Pat. No. 3,852,157 of Rubenstein et al. and this technique relies on competition between analyte molecules and enzyme-labelled analyte analogs (the "reactant") for a receptor (the "specific binding partner") in the assay solution.

Further signal detection techniques include turbidimetry and nephelometry as described hereinbefore in relation to separation methods.

In general, besides the sample under evaluation, calibration samples with known transferrin contents will also be assessed in the performance of the assay method of the invention. Such determinations can be used to plot a calibration curve from which the transferrin content of the sample under evaluation may be determined. Preferably calibration samples having transferrin contents of up to 0.05 mg/ml (e.g. 0.002, 0.01, 0.02 and 0.03 mg/ml) will be used.

In the assay method of the invention the total transferrin content of the determined or separated fraction containing the target variants will preferably be determined. Using an algorithm as herein described this can then be used to determine with a high degree of accuracy the content of asialo- or disialo-transferrin, or CDT content of the sample. The content of asialo- or disialo-transferrin or CDT may be determined as a percentage of total transferrin. This may be a more precise marker for alcohol consumption than total transferrin, and a threshold value, for example 1%, may be set. Alternatively, the presence of any transferrin variant may be assessed as an actual concentration (i.e. a mass per unit volume).

Viewed from a further aspect, the invention provides a kit for a diagnostic assay according to the invention, said kit comprising:

means for subjecting a sample of body fluid to a determination step or separation method capable of producing or determining the content of a fraction substantially free from tri- and higher sialylated transferrins;

means for the detection of transferrin; and means for determining the content of any transferrin variant or combination of transferrin variants in a sample of body fluid subjected to said separation method or determination step.

Conveniently, the kit may also comprise a transferrin standard or standards for reference. Thus, in one preferred embodiment, the kit of the invention may comprise:

at least two transferrin solutions having known asialo- and disialo-concentrations;

means for subjecting a sample of body fluid to a separation method or determination step capable of producing or determining the content of a fraction substantially free from tri- and higher sialylated transferrins;

means for the detection of transferrin; and means for determining the content of any transferrin variant or combination of transferrin variants in a sample of body fluid subjected to said separation method or said determination step.

The invention will now be illustrated by the following non-limiting Examples and the accompanying figures in which.

EXAMPLE 1

Figure 1:
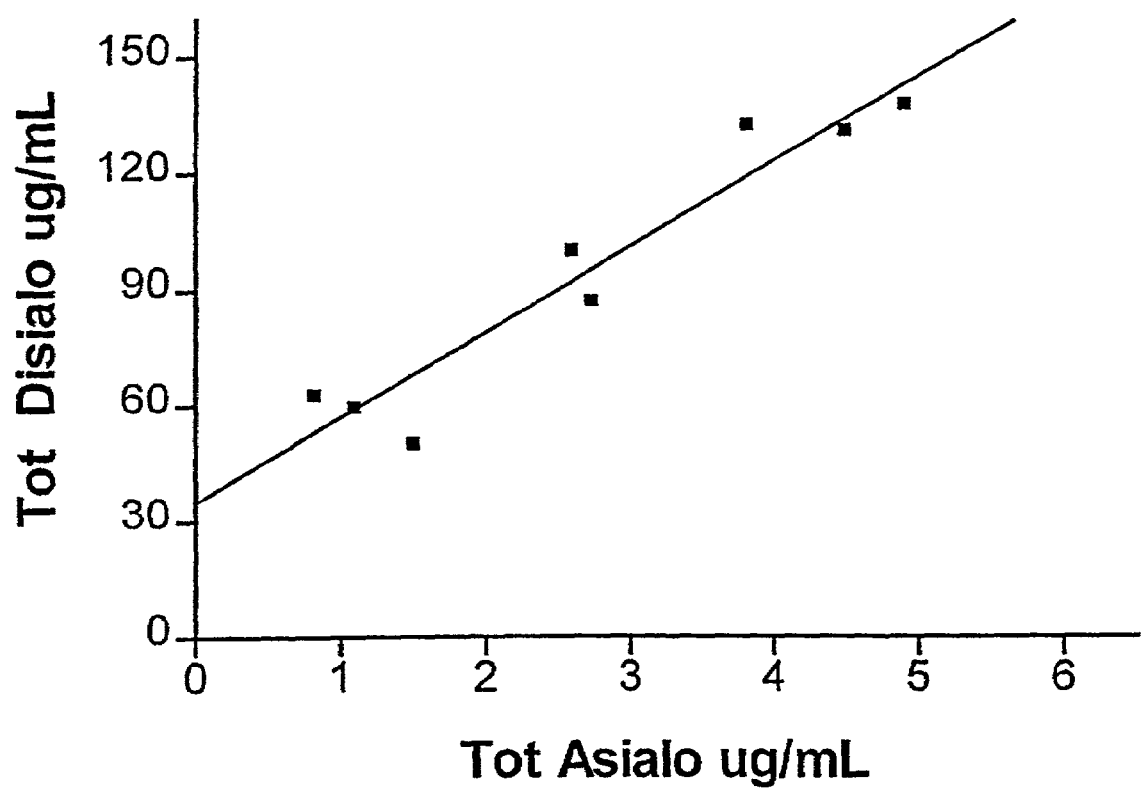
FIG. 1 shows the high correlation ($R^2=0.9153$) between the concentration of asialo- and disialotransferrin variants in a serum sample determined in accordance with the method of Example 1.

Reference Method—Determination of Asialo-, Monosialo-, Disialo- and Trisialo-Transferrin Content of Serum Samples The transferrin variant content of lipid stripped, iron treated serum samples was analysed using a combined HPLC-RIA method. The levels of the different sialic acid isoforms were determined first by separation on HPLC with an ion exchange column. The asialo-, monosialo-, disialo- and trisialotransferrin fractions were collected in separate tubes. The higher isoforms, tetrasialo-, pentasialo- and hexasialo-transferrins, were collected in a separate tube. The % of the different fractions was first determined using HPLC, then the concentration of the fractions was determined on a gamma counter using an immunoassay procedure as outlined below.

Reagents
Dextransulfate sodium salt
Calcium chloride dihydrate
Ferric chloride, $FeCl_3.6H_2O$, min. 99.0%
Acetic acid >99%
2-propanol
Nitrilotriacetic acid trisodium salt monohydrate >98%
BisTris(bis(2-hydroxyethyl)amino-tris(hydroxymethyl)methane)>99.5%
NaCl p.a.
2 M NaCl, p.a.
2 M NaOH, p.a.
5% Acetic acid
75% Acetic acid
Mobile phase A: 20 mM BisTris buffer, pH 6.5
Mobile phase B: 20 mM BisTris buffer, pH 6.5, 0.5M NaCl
Mobile phase C: 20 mM BisTris buffer, pH 5.8
Mobile phase D: water Equipment
  2 ml syringe
  0.2 µm filter for filtering serum samples (Gelman Acrodisc 13)
  Column: Pharmacia Resource Q 1 mL, Code 17-1177-01 or Pharmacia Source 15Q 1 mL
  Pre-column: HP Pre-column cartridge holder 4.0 mm inner diameter, filled with HQ50 in slurry form
  Transferrin, in solution and labelled with $^{125}I$
  Anti-transferrin antibody (raised in rabbit) solution
  Sheep anti-rabbit antibody (decanting solution)
  Calibrators 0, 5, 20, 50, 100 and 300 U CDT/L (1 U/L=0.034 µg/ml)
  Transferrin calibrators (based on Seronorm calibrated serum supplied by Sero AS, Norway, diluted in mobile phase A) 0, 0.05, 0.10, 0.15, 0.25, 0.50, 0.75, 1.0, 1.5, 2.5 µg/ml
  HPLC Degaser: Degaser Mod. G1322A
  HPLC Pump: Quaternary pump Mod. G1311A
  HPLC Injector: Autosampler Mod. G1313A, modified with a 900 µl injector loop
  HPLC Thermostat: Column thermostat Mod. G1316A, with a Reodyne multi-port
  HPLC Detector: Diode Array Detector Mod. G1315A
  Data Handling: HP ChemStation
  pH meter: Hanna Instruments 8417
  Centrifuge: Minifuge RF, Z-924
  Gamma counter: RIASTAR
  Fraction collector: GradiFRAC from Pharmacia

HPLC

150 µl of each serum sample was added to 30 µl FeNTA (an aqueous solution containing 2.751 g/l nitrilotriacetic trisodiummonohydrate and 2.703 g/l $FeCl_3.6H_2O$ adjusted to a pH of 6.5 using 2M NaOH) and vortexed. The resulting solution was then added to 10 µl dextran sulfate (20 mg/ml) and 10 µl potassium chloride (147 mg/ml). The solution was cooled to 2–8° C. for 30 mins. The sample was then centrifuged at 3800 rpm for 10 mins. 150 µl of the supernatant was pipetted out and added to 900 µl HPLC buffer A. The sample was filtered on an acrodisc filter and then injected into the HPLC in an aliquot of 800 µl. The transferrin isoforms were separated by an ion-chromatographic gradient method. The transferrin was selectively detected spectrophotometrically at 470 nm by the HP ChemStation.

Five fractions of the transferrin were collected from the HPLC into tubes in exact amounts. The fractions asialo- to trisialotransferrin were collected separately. The tetrasialo- to hexasialotransferrin were collected as a separate fraction. The asialo- and monosialo-fractions were not further diluted. The disialo- and trisialo-fractions were diluted 1:1 and the fraction containing the tetrasialo- to hexasialotransferrins was diluted 1:4 with mobile phase A.

To quantify the transferrin content of each isolated eluted fraction, the steps D1–D8 in the following immunoassay procedure were performed. In relation to the asialo fraction, in D8 the concentration was determined using calibrators from 0–2.5 µg/ml. In relation to the remaining fractions the steps D1–D8 were performed with the CDTect-calibrators.

Immunoassay Procedure

D1: 500 µl calibrator is pipetted out. The calibrators are dilutions of human transferrin (obtained from Intergen) in PBS containing 1% BSA, 0.1% Tween 20 at pH 7.0)

D2: 500 µl sample is pipetted out

D3: 50 µl transferrin $^{125}I$ is added to the sample. The $^{125}I$ transferrin solution is made by dilution of $^{125}I$ labelled human transferrin (obtained from Isopharma AS, Kjeller, Norway) to a concentration suitable for gamma-counting in an aqueous buffered solution containing 0.037 M disodiumhydrogen phosphatedihydrate, 0.013 M sodiumdihydrogen phosphatemonohydrate, 1% BSA, 0.1% Tween 20 and 0.03% Patent Blue.

D4: 50 µl antibody is added. The antibody solution is made from rabbit anti human transferrin antiserum (obtained from BioCell, product No. 01090) diluted 1:450 in 0.4 M sodium phosphate buffer with it BSA, 0.1% Tween 20 at pH 7.0.

D5: 2000 µl decanting suspension is added. The decanting suspension is a solution of secondary anti rabbit antibodies (obtained from Pharmacia & Upjohn, product No. 30–3794–00)

D6: incubate for 1 hour

D7: centrifuge 10 mins at 1500× g and remove supernatant

D8: determine radioactivity

The concentration and % distribution of transferrin variants determined in a given serum sample is shown in Table 1 below (150 µl serum is diluted to 1.1 ml and 800 µl is injected on the HPLC; dilution factor: 1.1/0.15*1/0.8=9.17):

TABLE 1

|  | asialo | mono- | di- | tri- | tetra & higher |
|---|---|---|---|---|---|
| HPLC fraction volume (ml) | 4 | 2.5 | 5 | 5.5 | 27.5 |
| Sample volume (µl) | 500 | 500 | 250 | 250 | 125 |
| Conc. in RIA sample (µl/mg) | 0.29 | 0.29 | 0.87 | 1.20 | 2.85 |
| Conc. corrected for sample volume (µl/mg) | 0.29 | 0.29 | 1.73 | 2.41 | 11.41 |
| Conc. per ml fraction (µg/ml) | 1.14 | 0.73 | 8.67 | 13.24 | 313.66 |
| Conc. in serum (µl/mg) | 10.47 | 6.66 | 79.50 | 121.45 | 2876.26 |
| % CDT-RIA | 0.34 | 0.22 | 2.57 | 3.92 | 92.95 |

EXAMPLE 2

Correlation Between Asialo- and Disialotransferrins and Lack of Monosialotransferrin Using the HPLC/RIA method described in Example 1, monsialotransferrin levels were found to be very low. In addition, asialo- and disialotransferrin levels were found to correlate as follows:

$$D=A.a+b$$

(wherein
D represents disialotransferrin content of a serum sample;
A represents asialotransferrin content of a serum sample;
a=22.2; and
b=36 mg/l)

This represents a squared correlation coefficient of 0.9153 (see attached FIG. 1).

Using relative units (t total transferrin coefficients), the following values for a and b were determined:
a=22.25
b=1.05% (0.0105)

Figure 2:
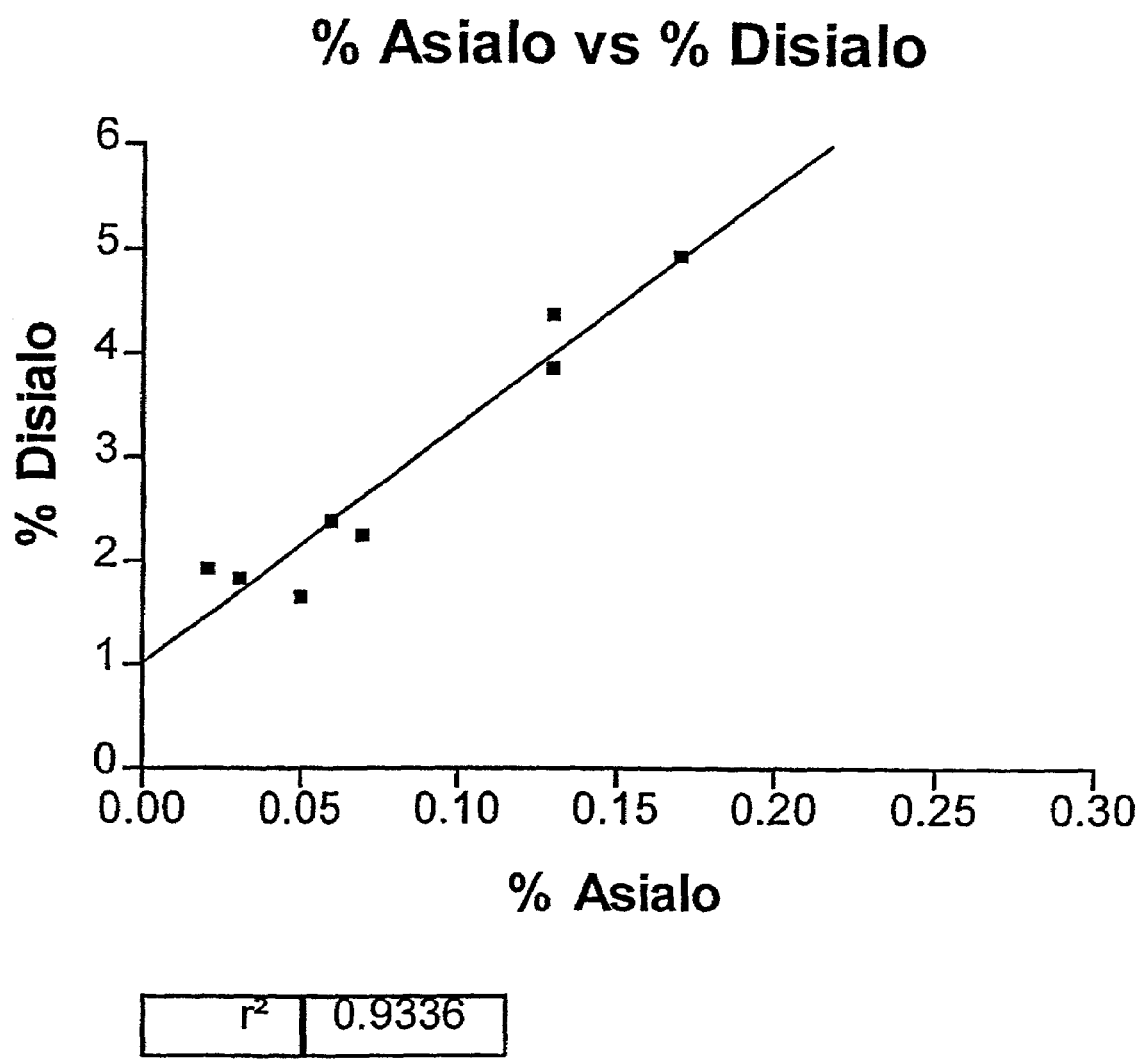
FIG. 2 shows the high correlation ($R^2$ 0.9336) between the % of asialo- and disialotransferrin variants in a serum sample determined in accordance with the method of Example 1.

This represents a squared correlation coefficient of 0.9336 (see attached FIG. 2).

EXAMPLE 3

Determination of Algorithm to Calculate Levels of Asialotransferrin, Disialotransferrin and CDT in a Serum Sample At least two solutions having known levels of asialo- and disialotransferrins are subjected to a separation method capable of removing substantially all tri- and higher sialotransferrins (e.g. based on lectins or ion exchange matrices). Thereafter the total transferrin content of the isolated fraction of transferrin is determined (e.g. by a radioimmunoassay method for transferrin quantitation). Based on the previously determined correlation between the level of asialo- and disialotransferrins and the low level of monoasialotransferrin, the following relations can be established:

$$T1=c.A1+d.D1$$

$$T2=c.A2+d.D2$$

$$T3=c.A3+d.D3$$

etc.

(wherein
T1, T2, T3, etc. represent the measured total transferrin content of each sample following separation*;
* these may be measured in mass units or relative to the total transferrin content of the sample.
A1, A2, A3, etc. represent the known contents of asialotransferrin in each sample;
D1, D2, D3, etc. represent the known contents of diasialotransferrin in each sample; and c and d are constants).

Calculation of the Content of Asialotransferrin, Diasialotransferrin and CDT in any Sample from the Partial Measurement of T:

For any sample tested:

$$T=c.A+d.D$$

and $$D=a.A+b$$

(wherein
T represents measured total transferrin content;
A represents actual asialotransferrin content in the sample;
D represents actual disialotransferrin content in the sample; and
a, b, c and d are each constants).

It follows that:

$$A=(T-d.b)/(c+d.a);$$

$$D=b+a(T-d.b)/(c+d.a); \text{ and}$$

$$CDT=A+D=b+(a+1)(T-d.b)/(c+d.a)$$

(where CDT is the total content of asialo-, monosialo- and disialotransferrin in the sample).

EXAMPLE 4

Quantitation of Transferrin Content by Means of Anion Exchange and Lectin Binding 20 µl of a serum sample is mixed with 50 µl of a solution of 10 mM bis-tris, 3.1 mM sodium azide, 0.05% Tween 20, 1 M HCl ad pH 7.0, 0.8 mM Tris base, 0.15 mM FeCl3, 0.15 M sodium citrate and 0.4 mM maleic acid. The resulting solution is added to 0.5 ml of 25% preswollen Whatman QA52 ion exchange resin suspended in 20 mM Bis-Tris buffer ((2-hydroxy)amino-tris(hydroxymethyl)methane) pH=6.3. The chloride content of the medium is carefully adjusted to retain substantially all transferrin molecules with more than two sialic acid residues (this may be monitored by HPLC or isoelectric focusing). Thereafter, 0.25 ml of a 25% suspension elderberry bark lectin (Vector Laboratories, US) is added (this ensures a more complete mopping up of sialylated transferrin molecules), and the suspension is mixed gently. The suspension is thereafter filtered by centrifugation in a Millipore Ultra-Free UFC3 OHV filter cup, and the filtrate is collected. 200 µl of the filtrate is mixed with 200 µl of a transferrin antibody (Dako) solution diluted 1:10 in 0.27 M Tris, 4.5% PEG 8000, 4.3 mM sodium azide pH=7.4. The concentration of transferrin in the filtrate is determined by interpolating the nephelometric signal in a standard curve constructed from standards of known concentrations of human transferrin.

With this separation method, c 0.93 and d=0.45.

EXAMPLE 5

Quantitation of Transferrin Content by Means of Anion Exchange

20 µl of a serum sample is mixed with 50 µl of a solution of 10 mM bis-tris, 3.1 mM sodium azide, 0.05% Tween 20, 1 M HCl ad pH 7.0, 0.8 mM Tris base, 0.15 mM FeCl3, 0.15 M sodium citrate and 0.4 mM maleic acid. The resulting solution is added to 0.5 ml of 25% preswollen Whatman QA52 ion exchange resin suspended in 20 mM Bis-Tris buffer ((2-hydroxy)amino-tris(hydroxymethyl)methane) pH=6.3. The chloride content of the medium is carefully adjusted to retain substantially all transferrin molecules with more than two sialic acid residues (this may be monitored by HPLC or isoelectric focusing). The suspension is thereafter filtered by centrifugation in a Millipore Ultra-Free UFC3 OHV filter cup, and the filtrate is collected. 200 µl of the filtrate is mixed with 200 µl of a transferrin antibody (Dako) solution diluted 1:10 in 0.27 M Tris, 4.5% PEG 8000, 4.3 mM sodium azide pH=7.4. The concentration of transferrin in the filtrate is determined by interpolating the nephelometric signal in a standard curve constructed from standards of known concentrations of human transferrin.

EXAMPLE 6

Quantitation of Transferrin Content by Means of Immobilised Lectin from Sambuccus nigra in a Column Format.

a. 10 µl serum samples are mixed with 0.5 ml binding buffer 20 mM Tris-HCl buffer with pH=7.5 containing 150 mM sodium chloride.

b. Each diluted serum sample is passed through a column of 0.5 ml agarose elderberry bark (Sambuccus nigra) lectin (supplied by Vector Laboratories, Burlingame, USA) suspended in 20 mM Tris-HCl buffer with pH=7.5 containing 150 mM sodium chloride, and another 1.0 ml of the same buffer is passed through the column.

c. Mix 200 µl of the eluted solution with 200 µl of an anti-transferrin antibody solution comprising 0.27 M Tris, 4.5% PEG 8000, 4.3 mM sodium azide, 1:10 dilution of Dako anti-human-transferrin antibodies Q0327, and HCl to pH=7.4.

d. Read the turbidimetric/nephelometric signal.

With this separation method, c=0.98 and d 0.08.

EXAMPLE 7

Equipment
  Columns (7 mm internal diameter) containing 0.5 ml POROS HQ50 (Perseptive Biosystems) between polyethylene upper and lower porous frits (Porex, Atlanta, Ga., USA)—columns available from Pierce Company, USA
  Four calibrators**
    ** Prepared using human normal serum. See Table 2 for dilutions
  Pipettes covering volumes from 4 µl to 3 ml Alternatively: multipipettes for volumes 100 µl, 200 µl, 2 ml and 3 ml
  Racks (for tubes (75×12 mm)
  Microtiter plates
  Reader for microtiter plates, 405 nm filter

TABLE 2

| Calibrators (mg/ml) | Human normal serum containing 2.17 mg transferrin/ml | Solution 2 |
| --- | --- | --- |
| C1: 0.002 | 100 µl C3 | 900.0 µl |
| C2: 0.01 | 4.6 µl | 995.4 µl |
| C3: 0.02 | 10.1 µl | 1089.9 µl |
| C4: 0.03 | 13.8 µl | 986.2 µl |

(Calibrator C1 is produced by dilution of calibrator C3 with Solution 2).

Reagents—Solution 1
  10 mM BisTris (bis(2-hydroxyethyl)amino-tris-(hydroxymethyl)methane)
  3.1 mM Sodium Azide
  0.05% Tween 20
  1M HCl ad pH 7.0
  0.8 mM Tris base (Tris(hydroxymethyl)aminomethane)
  0.15 mM $FeCl_3$
  0.15 mM Sodium Citrate
  0.4 mM Maleic acid
  deionized $H_2O$ q.s.

Solution 2
  50 mM BisTris (bis(2-hydroxyethyl)amino-tris-(hydroxymethyl)methane)
  3.1 mM Sodium Azide
  0.05% Tween 20
  1M HCl ad pH 6.00
  approx 3 mM Na Cl added
  deionized $H_2O$ q.s.

Turbidimetric Reagent
  900 µl 0.3M Tris/PEG pH 7.4
  1001 µl Rabbit anti-serum transferrin (Dako)
  The 0.3M Tris/PEG pH 7.4 comprises:
  0.3 m Tris. HCl
  6% Polyethylene glycol (PEG 8000)
  3.1 mM Sodium Azide
  2M NaOH ad pH 7.4
  deionized $H_2O$ q.s.

Preparation of Columns:
  Use one column for each sample to be tested. Elute surplus transport buffer by removing first the top and thereafter the bottom stopper, discard and eluate. Prepared columns should be used within 2 hours.

Sample Testing Procedure
  Sample Procedure
    1. Add 100 µl serum to 500 µl solution 1 in a test tube. Mix.
    2. Incubate for 5–10 minutes at ambient temperature.
  Column Separation
    1. All solutions added must elute freely from the column.
    2. Add 500 µl incubated sample to a column.
    3. Let the sample sink into the top filter before adding 1.0 ml of solution 2.
    4. Let solution 2 sink into the top filter. Change tubes below columns. Solution eluted up to this point should be discarded. Add 2.0 ml of solution 2 to each column. Collect 2 ml eluate 2.
  Measurement
    1. Add 200 µl of each calibrator, and 200 µl of eluate 2 from the column separation to separate wells of a microtiter plate. Read at 405 nm.
    2. Add 100 µl turbidimetric reagent to each well.
    3. Incubate for 15 minutes at ambient temperature.
    4. Read results using a reader with 405 nm filter and subtract the background calculated in step 1.
    5. Establish a calibration curve using non-linear regression.
    6. transferrin content in the serum sample is calculated from the calibration curve.

With this separation method, c=0.98 and d=0.66.

EXAMPLE 8

Determination of Asialo- and Disialo-transferrin, and a Combination of Asialo-, Monosialo- and Disialo-transferrin, Using a Combined HPLC-RIA Method.

A further experiment was carried out to determine the correlation between
  1) asialo- and monosialo-transferrin isoforms in serum samples,
  2) asialo- and disialo-transferrin isoforms in serum samples, 3) (asialo-, monosialo- and disialo-) and asialo-transferrin isoforms in serum samples, and
4) (asialo-, monosialo- and disialo-) and disialo-transferrin isoforms in serum samples.

These experiments were carred out to test the reliability of the relationship between the content of asialo-, mono sialo- and disialo-transferrins (in the above combinations 1–4) in serum samples from a number of different individuals.

Reagents, Materials, Instruments and Equipment

The experiment was carried out using the same reagents, materials, instruments and equipment as described in Example 1.

Experimental

Transferrin in lipid stripped, iron treated serum was analysed on two combined methods, HPLC and RIA. The different sialic acid isoforms were determined, first by separation on a HPLC with a ion exchange column. The % of the different fractions are first determined on the HPLC, then the concentration of the fractions are determined on a gamma counter by using parts of the CDTect™

Results and Discussion

Fourteen samples of serum were collected from 14 individuals and in each of these samples, the asialo-, mono- and disialo-transferrin fractions were separated and collected individually. For each sample, the concentration of each fraction was determined as percentage of total transferrin using the RIA method (% CDT-RIA) and HPLC method (% CDT-HPLC) as described in Example 1. The concentration of the asialo-, mono- and di-sialo transferrin was also determined in μg/mL for the RIA method (CDT RIA μg/ML). These results are shown below in Table 3.

Figure 5A:
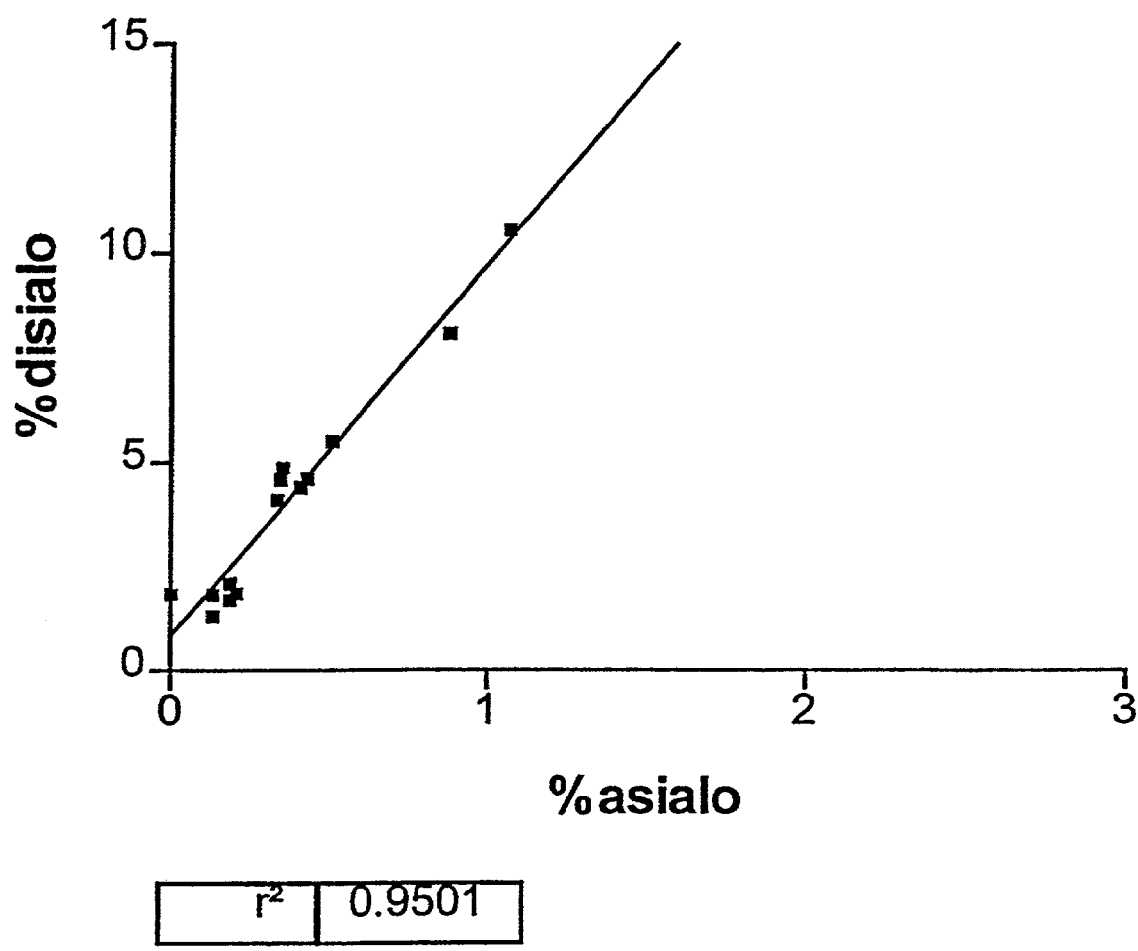
FIGS. 5A and 5B show correlation of asialo vs disialo, in A determined in % transferring in B determined in μg/mL.
Figure 5B:
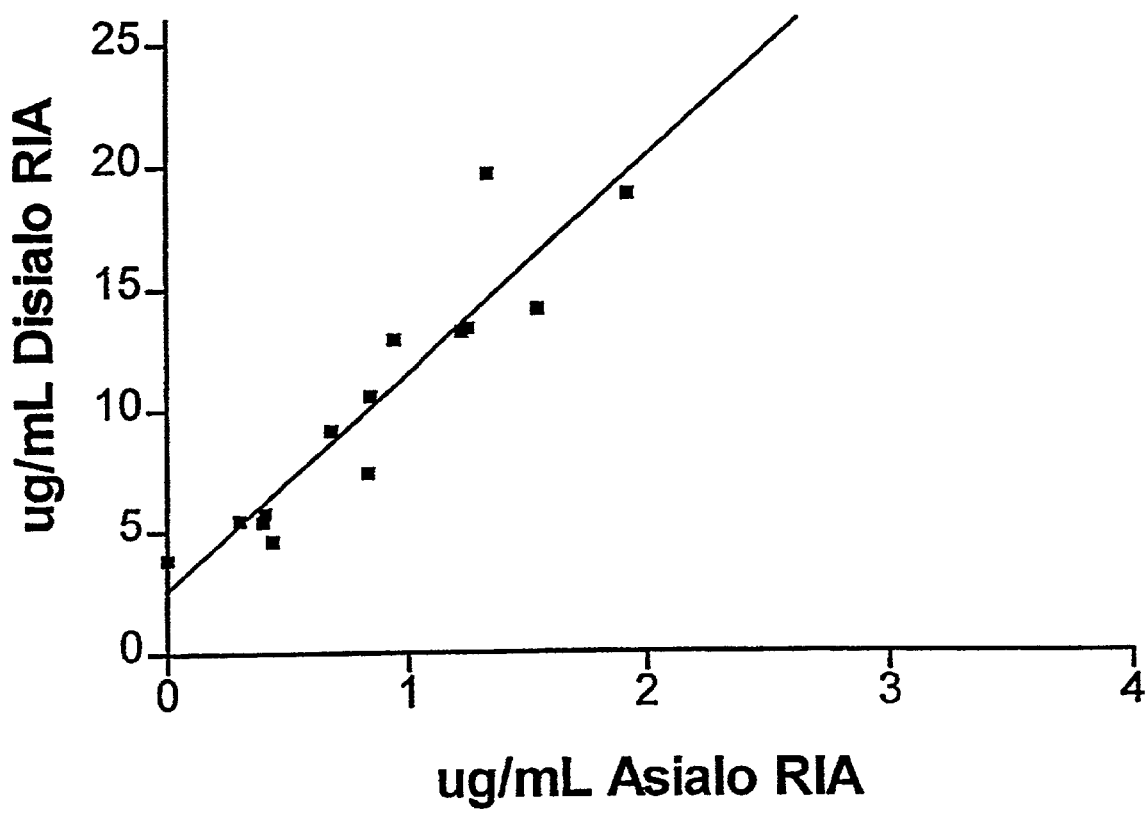

FIGS. 5A and 5B show correlation of asialo vs disialo, in A determined in % transferrin, in B determined in μg/mL. The graphs are produced using data from teh RIA method.

The squared correlation coefficient based on percentage determination (relative units) was 0.9501 (see FIG. 5a). Based on mass units (FIG. 5B) the squared correlation coefficient was 0.8603.

The correlation of asialo- vs disialo-transferrin was as expected better for the % determination than for μg/mL. This is due to the correction for high and low total transferrin for high and low total transferrin content, in the % isoform determination.

Figure 6:
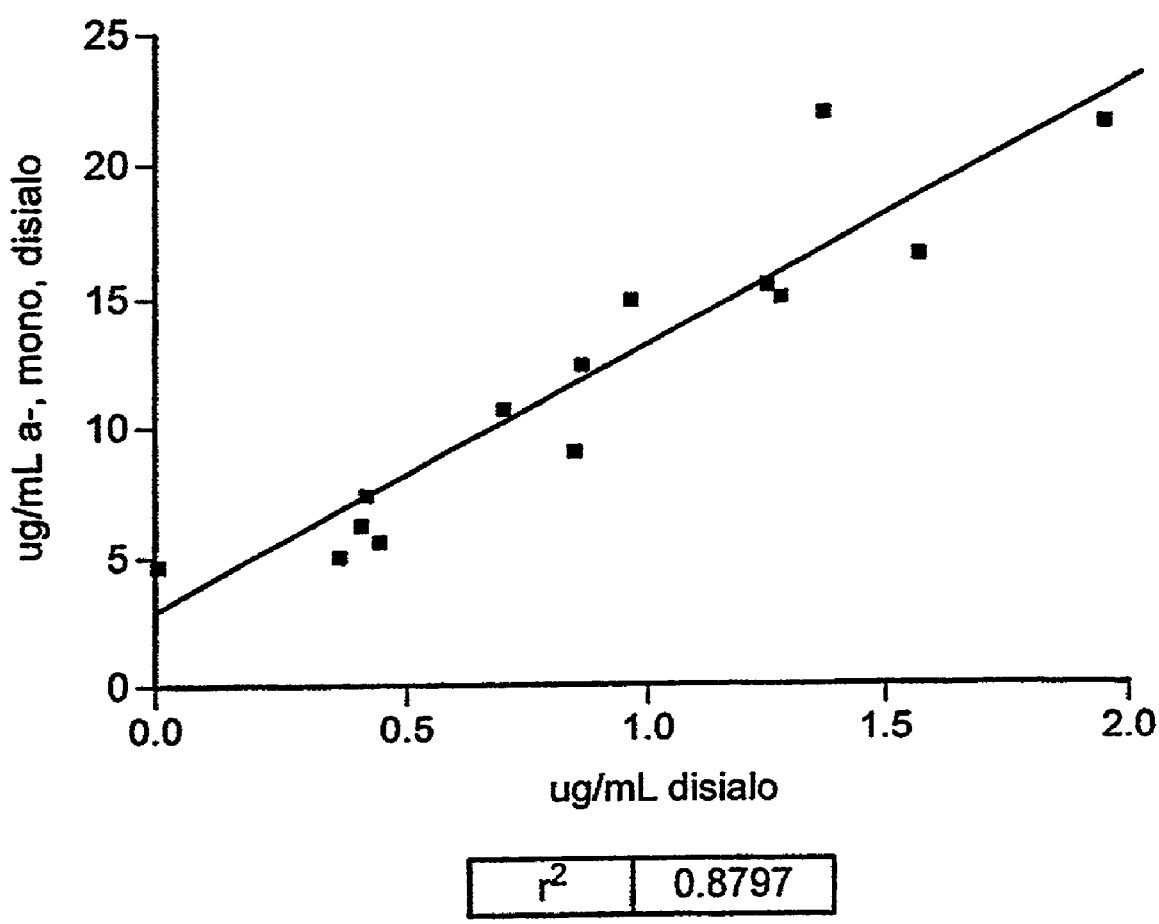
FIG. 6 shows the correlation of (asialo-, monosialo- and disialo-transferrin) with asialo transferring determined in mass units (μg/mL).

FIG. 6 shows the correlation of (asialo-, monosialo- and disialo-transferrin) with asialo transferrin, determined in mass units (μg/mL). The squared correlation coefficient was 0.8797. The graph is produced using data from the RIA method.

Figure 7:
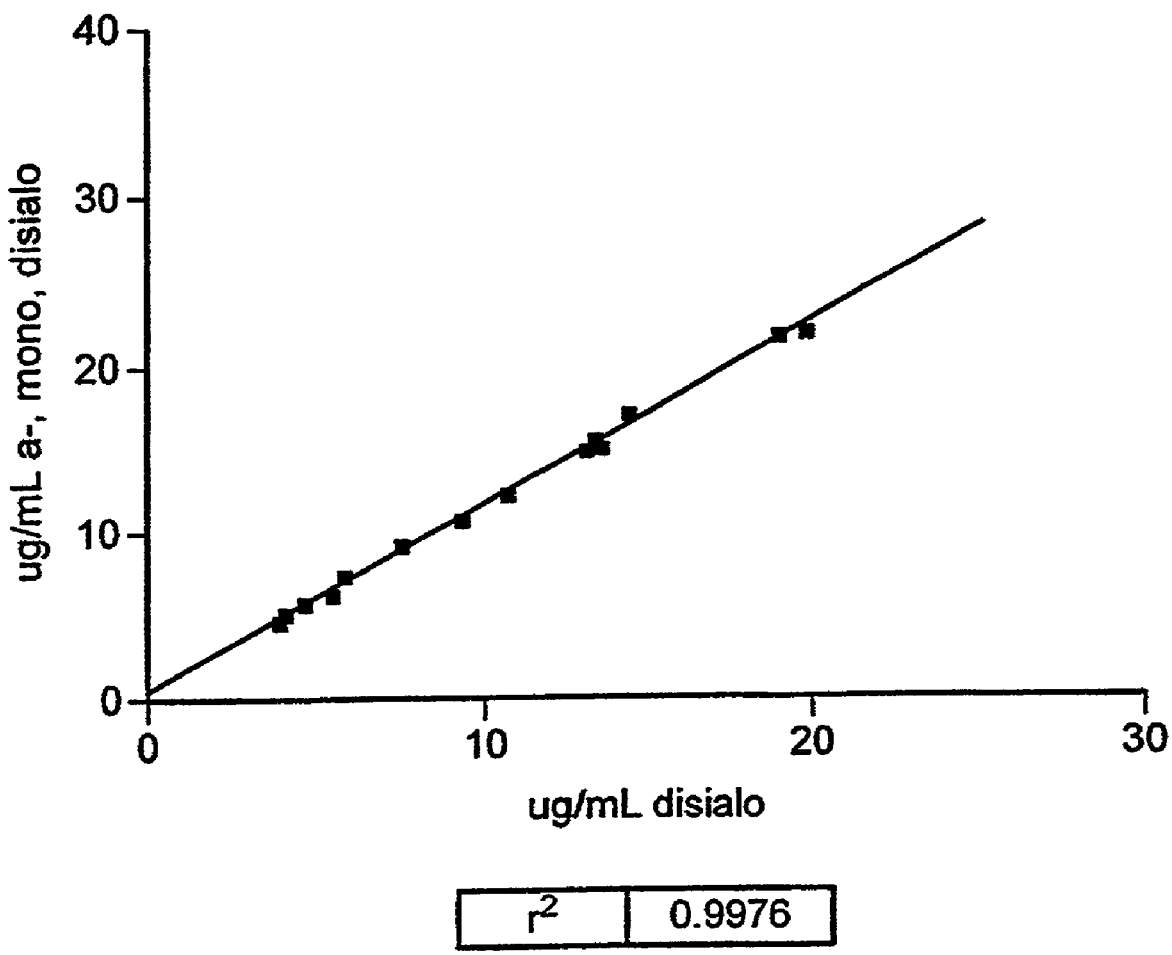
FIG. 7 shows the correlation of (asialo-, monosialo- and disialo-transferrin) with disialotransferrin, determined in mass units (μg/mL).

FIG. 7 shows the correlation of (asialo-, monosialo- and disialo-transferrin) with disialotransferrin, determined in mass units (μg/mL). The squared correlation co-efficient was 0.9176. The graph is produced using data from the RIA method.

At present, the precision of asialotransferrin determination is lower than e.g. disialotransferrin (due to much lower concentration), and therefore the correlation coefficient for asialotransferrin is lower. However the correlation coefficient for asialotransferrin is much higher than had previously been thought possible.

TABLE 3

| | % CDT-RIA | | | | | % CDT-HPLC | | | | | | CDT RIA μg/mL | | |
|---|---|---|---|---|---|---|---|---|---|---|---|---|---|---|
| | Asialo | mono | di | tri | tetra+ | Asialo | mono | di | tri | tetra | penta | Asialo | mono | di |
| CSB | 0.18 | 0.3 | 1.69 | 5 | 92.82 | 0 | 0.15 | 1.28 | 5 | 75.48 | 18.1 | 0.4 | 0.52 | 5.4 |
| MCDT | 0.34 | 0.49 | 4.6 | 7.04 | 87.52 | 0.18 | 0.15 | 2.82 | 5.39 | 72.24 | 19.22 | 0.68 | 0.77 | 9.2 |
| O4 | 0.18 | 0.43 | 2.08 | 8.46 | 88.84 | 0 | 0.24 | 1.32 | 7.02 | 76.59 | 14.82 | 0.36 | 0.65 | 4.04 |
| 123 | 0.33 | 0.39 | 4.11 | 6.77 | 88.41 | 0.19 | 0.14 | 2.86 | 6.98 | 59.42 | 30.42 | 0.84 | 0.99 | 10.6 |
| O2 | 1.07 | 0.7 | 10.6 | 8.07 | 79.59 | 0.93 | 0.38 | 9 | 8.8 | 58.92 | 21.98 | 1.92 | 1.24 | 18.9 |
| 122 | 0.43 | 0.22 | 4.61 | 6.42 | 88.32 | 0.35 | 0.14 | 3.89 | 5.24 | 67.37 | 23.02 | 1.26 | 0.64 | 13.4 |
| k7 | 0.13 | 0.39 | 1.82 | 9.93 | 87.74 | 0.03 | 0.37 | 1.75 | 8.41 | 68.23 | 21.21 | 0.41 | 1.23 | 5.76 |
| 126 | 0.51 | 0.34 | 5.52 | 4.46 | 89.17 | 0.53 | 0.15 | 5.32 | 3.92 | 63.32 | 26.76 | 1.34 | 1.22 | 19.7 |
| 127 | 0.2 | 0.22 | 1.84 | 4.66 | 93.07 | 0.16 | 0.17 | 1.92 | 4.49 | 68.87 | 24.4 | 0.83 | 0.9 | 7.44 |
| SBL | 0 | 0.41 | 1.83 | 5.13 | 92.63 | 0 | 0.14 | 0.92 | 4.12 | 76.79 | 18.03 | 0 | 0.85 | 3.84 |
| 129 | 0.41 | 0.45 | 4.41 | 4.37 | 90.37 | 0.35 | 0.19 | 4.59 | 3.99 | 67.42 | 23.47 | 1.23 | 1.34 | 13.2 |
| 130 | 0.88 | 0.71 | 8.09 | 7.2 | 83.13 | 0.91 | 0.24 | 7.32 | 6.94 | 70.01 | 14.58 | 1.55 | 1.25 | 14.2 |
| 136 | 0.13 | 0.19 | 1.3 | 1.34 | 97.04 | 0 | 0.13 | 1.04 | 4.63 | 72.96 | 21.25 | 0.44 | 0.66 | 4.6 |
| 125 | 0.35 | 0.49 | 4.87 | 7.16 | 87.13 | 0.11 | 0.27 | 3.23 | 7.48 | 68.8 | 20.12 | 0.94 | 1.3 | 12.9 |

Figure 3:
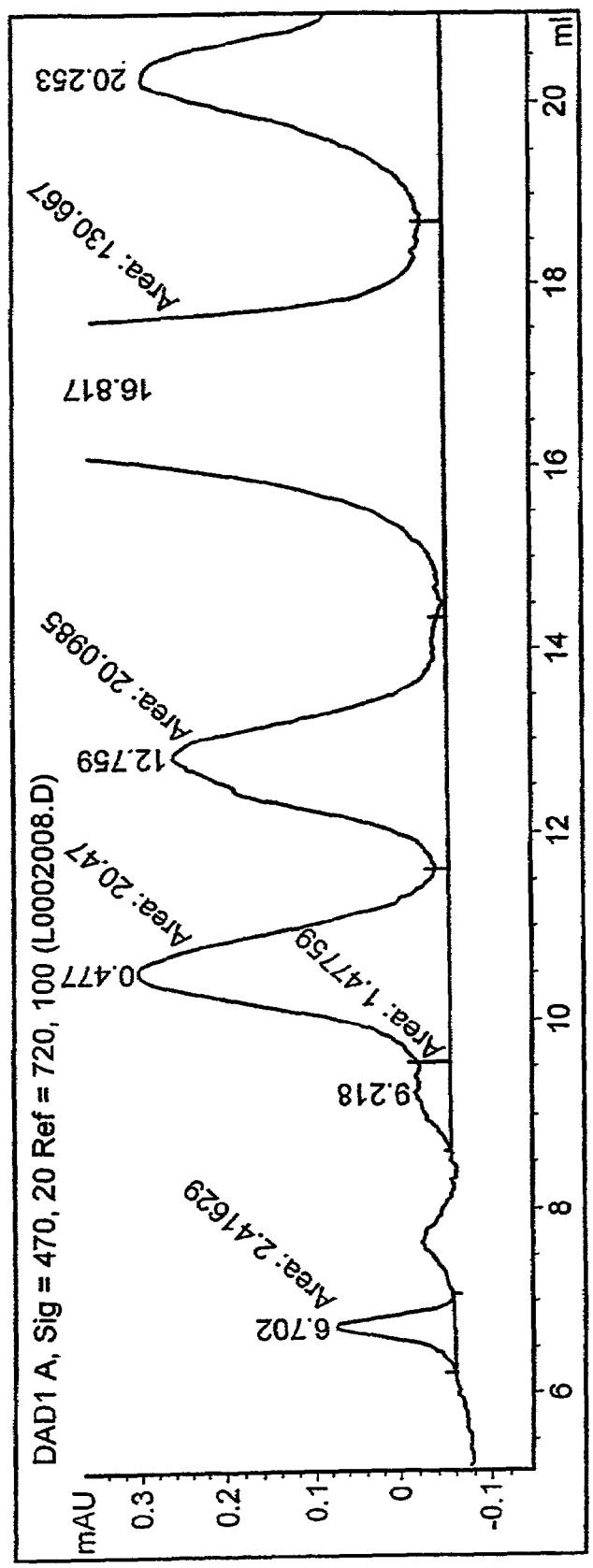
FIG. 3 shows separation of transferrin isoforms by HPLC.

FIG. 3 shows separation of transferrin isoforms by HPLC. The separation of monosialo and disialo is not complete, as can be seen between 9 and 10 min.

Figure 4A:
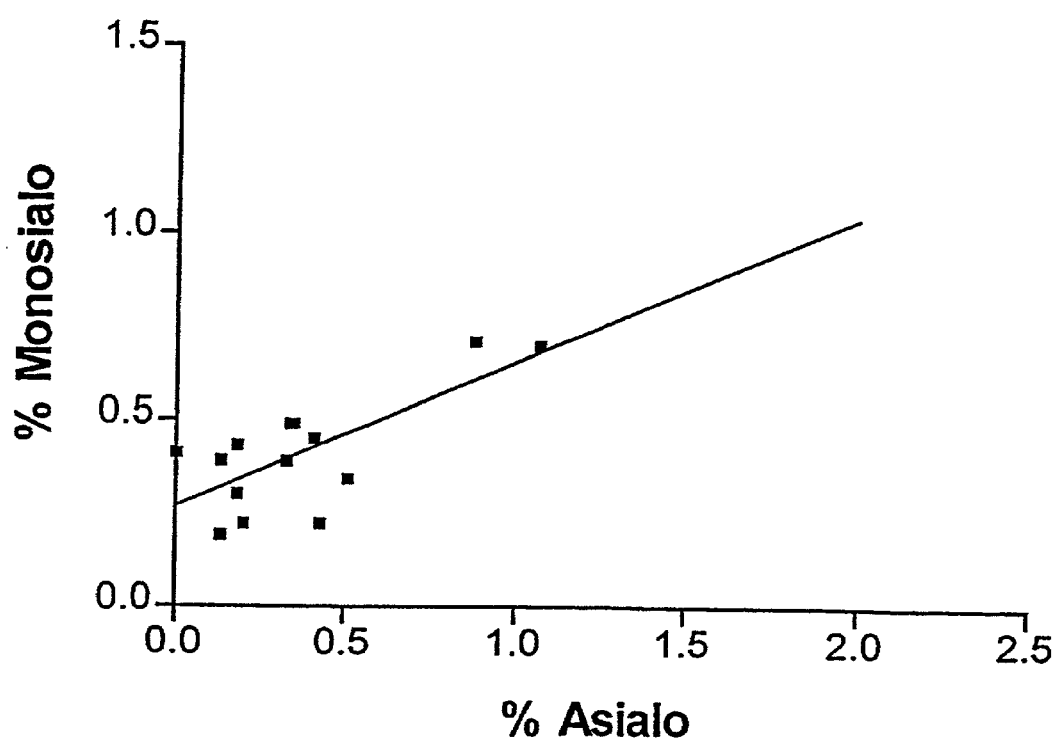
FIGS. 4A and 4B show correlation of asialo vs monosialo, in A determined in t transferring in B determined in μg/mL.
Figure 4B:
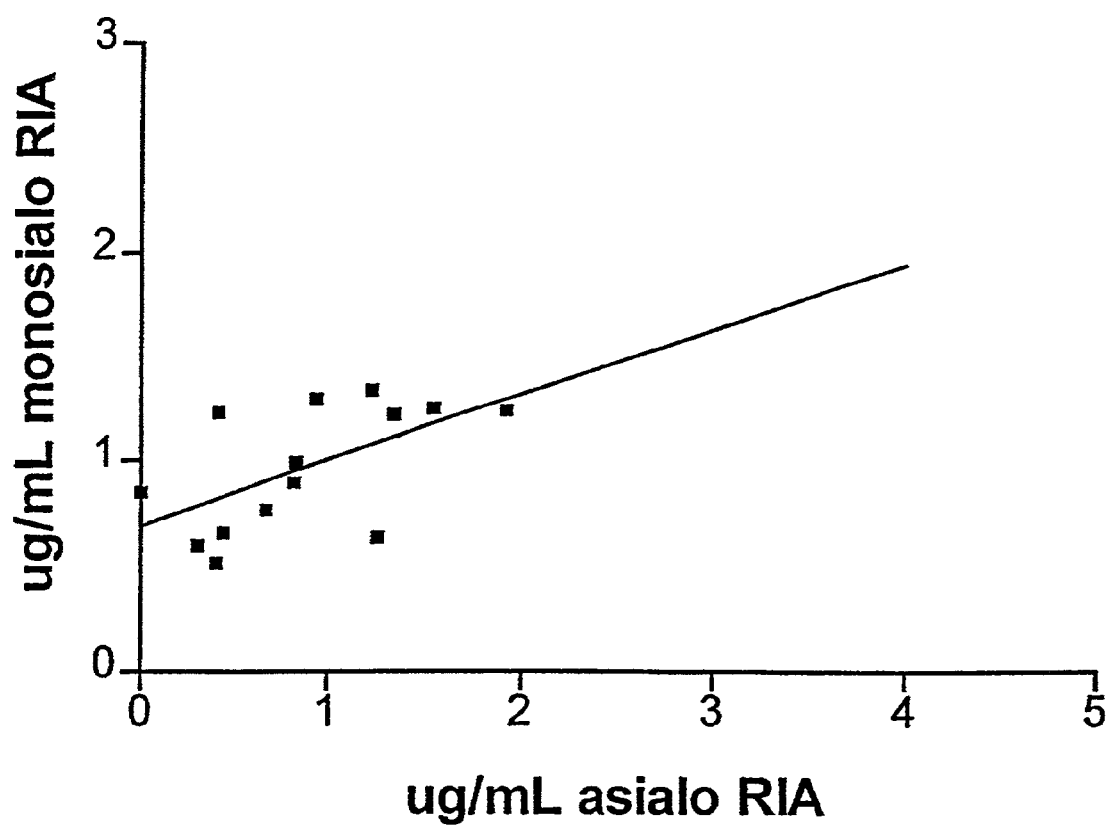

FIGS. 4A and 4B show correlation of asialo vs monosialo, in A determined in % transferrin, in B determined in μg/mL. The squared correlation coefficient based on percentage determinations (FIG. 4A) was 0.5235. Based on mass units (FIG. 4A) the squared correlation coefficient was 0.3339. The graphs are produced using data from the RIA method.

Hence the asialo vs monosialo transferrin did not show a good correlation for either of the determinations. One of the reasons for this might be that for the higher asialo values the disialo peak seems to overlap the monosialo. This can be seen in FIG. 3.

EXAMPLE 9

Determination of Asialo, Monosialo, Disialo and Trisialo, and Combinations of Asialo, Monosialo and Disialo Transferrin, Using a Combined HPLC-RIA Method.

A further experiment was carried out to determine the correlation between 1) asialo- and (monosialo- and disialo-) transferrin isoforms in serum samples,
2) asialo- and trisialo-transferrin isoforms in serum samples,
3) (asialo-, monosialo- and disialo-) and asialo-transferrin isoforms in serum samples, and 4) (asialo-, monosialo- and disialo-) and disialo-transferrin isoforms in serum samples.

These experiments were carred out to test the reliability of the relationship between the content of asialo-, mono sialo- and disialo-transferrins (in the above combinations 1–4) in serum samples from a number of different individuals.

Reagents, Materials, Instruments and Equipment

The experiment was carried out using the same reagents, materials, instruments and equipment as described in Example 1.

Experimental

Transferrin in lipid stripped, iron treated serum was analysed on two combined methods, HPLC and RIA. The different sialic acid isoforms were determined, first by separation on a HPLC with a ion exchange column. The % of the different fractions are first determined on the HPLC, then the concentration of the fractions are determined on a gamma counter by using parts of the CDTect™.

Results and Discussion

Twenty six samples of serum were taken from 26 individuals. However the mono- and disialo-transferrin fractions were collected together as a single fraction.

The concentrations of each fraction were determined by the RIA and HPLC methods respectively and the results are shown in Table 4 below:

CONCLUSION

From these Examples 8 and 9 it can be seen that there is a correlation between asialo and mono- & disialotransferrin, as well as between asialo- and disialo-transferrin and between either asialo- or disialo-transferrin and CDT (asialo-+monosialo-+disialo-transferrin). Important to notice is that the monosialo fraction is small compared to disialo and will therefore only give a small contribution in the correlation study. This indicates that both asialo and disialo isoforms of transferrin can be used as parameters for monitoring alcoholic diseases. Trisialo was not seen to give any correlation to asialo and is probably not a good marker. Hence the clinical value of the assay according to the invention has been demonstrated, and combinations of transferrin variants suitable for use in producing the algorithm according to the invention have been found.

Furthermore, Example 9 illustrates that complete separation of the disialo transferrin is not required because the presence of the monosialo-variant in the determined or separated fraction is not harmful to the correlation results.

The invention claimed is:

1. A method of producing an algorithm for determining the content of a transferrin variant or combination of trans-

TABLE 4

| | % CDT-RIA | | | | | % CDT HPLC µg/mL | | | | |
|---|---|---|---|---|---|---|---|---|---|---|
| | Asialo | m + di | tri | tetra | Penta | Asialo | m + di | tri | tetra | penta |
| Sample 1 | 1.5 | 12.1 | 5.5 | 63.2 | 17.8 | 1.3 | 11.7 | 4.6 | 63.4 | 19 |
| Sample 3 | 1.2 | 10.5 | 4.2 | 67.8 | 15.2 | 1.4 | 11.3 | 4.7 | 64.6 | 17.1 |
| Sample 8 | 0.5 | 3.7 | 6.3 | 73.5 | 16 | 0.6 | 3.8 | 6.1 | 72.8 | 16.7 |
| Sample 10 | 0 | 2 | 4.6 | 75.4 | 18 | 0.6 | 2.6 | 4.7 | 70.2 | 22 |
| Sample 12 | 0 | 2.6 | 3.1 | 70 | 24.4 | 0.4 | 3 | 3.1 | 64.7 | 28.8 |
| Sample 15 | 0.5 | 4.1 | 5.1 | 69.4 | 20.8 | 0.4 | 3.9 | 4.8 | 67.1 | 23.7 |
| Sample 17 | 0 | 1.6 | 6.12 | 76 | 16.3 | 0.5 | 1.3 | 5.7 | 77.6 | 14.9 |
| Sample 18 | 0 | 2.8 | 5.5 | 73.6 | 18.1 | 0.4 | 2.7 | 4.7 | 74.3 | 17.8 |
| Sample 20 | 0 | 2.9 | 5.4 | 73.3 | 18.4 | 0.2 | 3.1 | 4.9 | 72.4 | 19.4 |
| Sample 23 | 0.3 | 3.8 | 6 | 73.6 | 16.3 | 0.7 | 3.8 | 5.3 | 71.8 | 18.4 |
| Sample 25 | 0 | 1.5 | 2.2 | 74.1 | 22.2 | 0.5 | 1.5 | 2.2 | 75.6 | 20.3 |
| Sample 27 | 0.4 | 3.1 | 5.9 | 72 | 18.5 | 0.8 | 3.4 | 5.6 | 71.3 | 18.9 |

Figure 8:
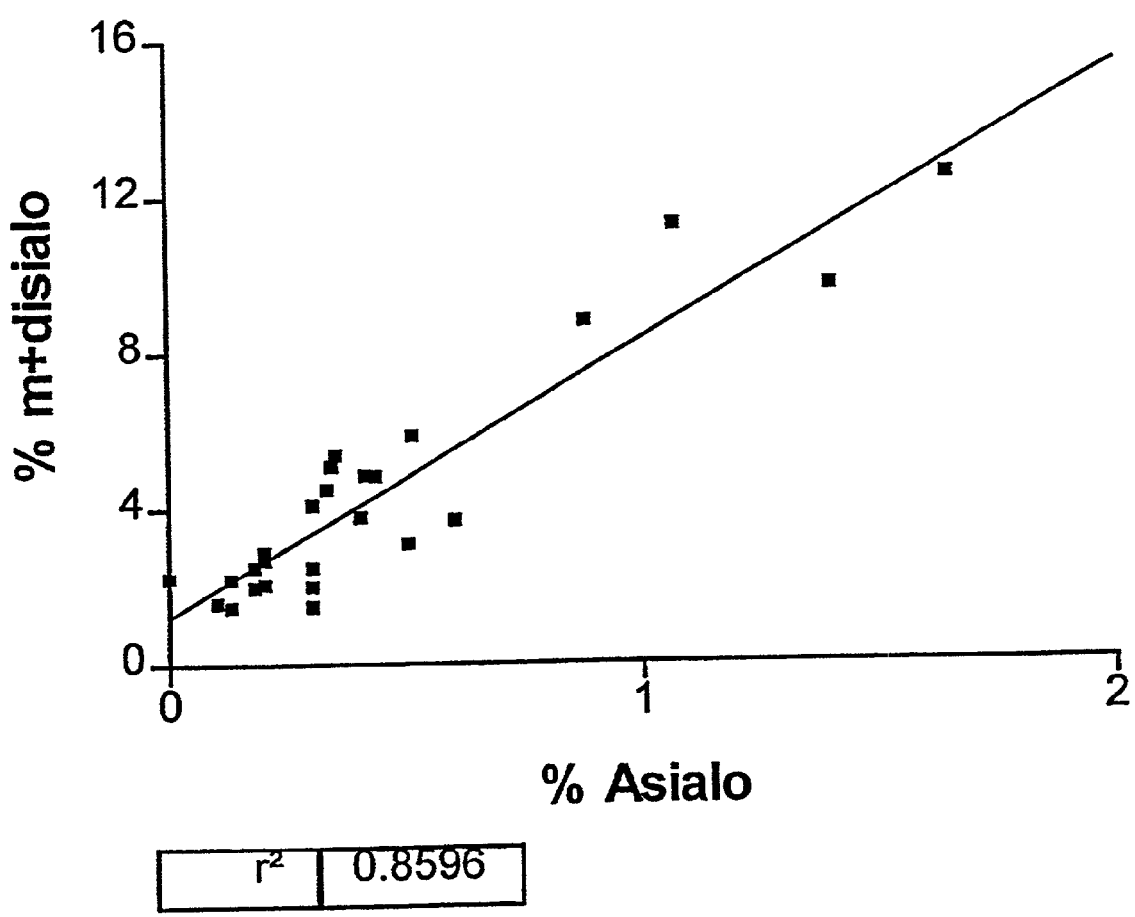
FIG. 8 shows the correlation of asialo transferrin with (monosialo- and disialo-) transferring determined in % transferrin.

FIG. 8 shows the correlation of asialo transferrin with (monosialo- and disialo-) transferrin, determined in % transferrin. A reasonable correlation was found. The squared correlation coefficient was 0.8596. The graphs are produced using data from the RIA method.

Figure 9:
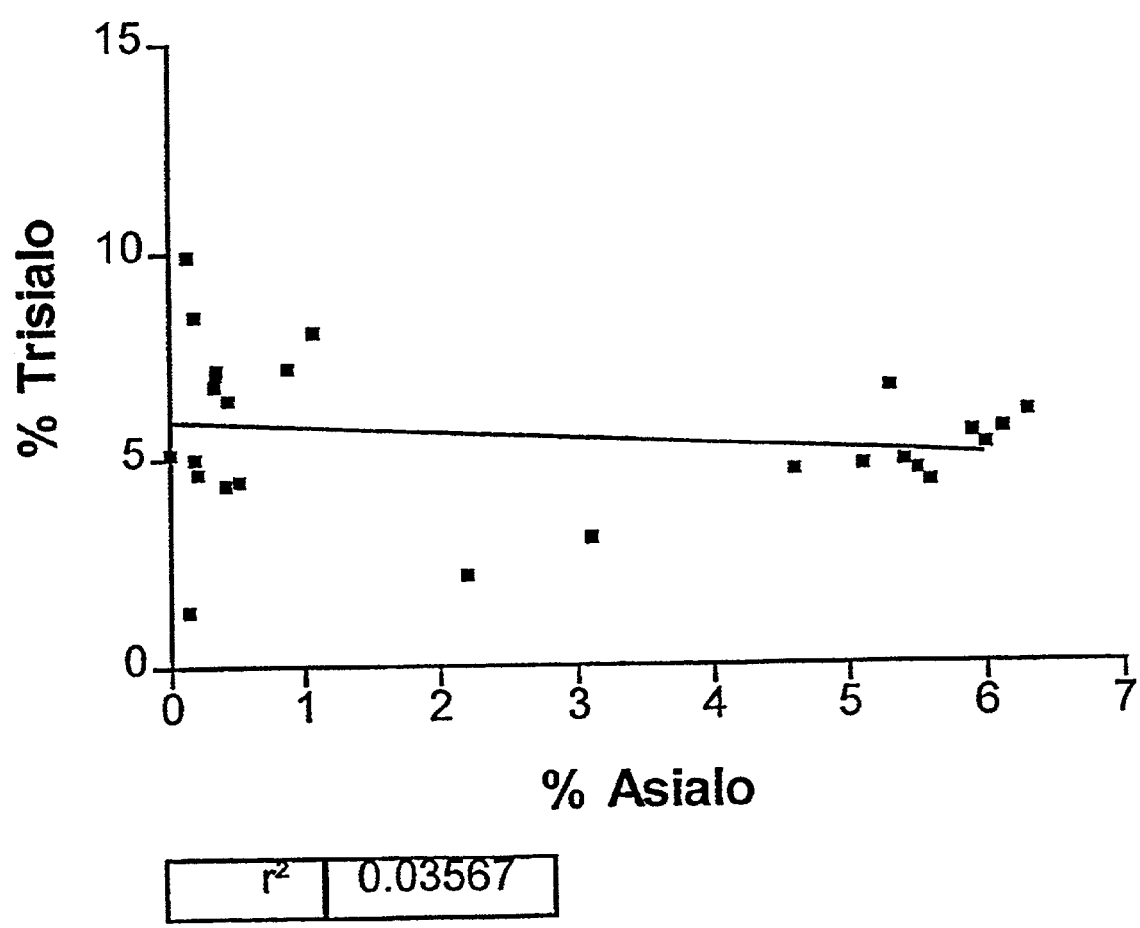
FIG. 9 shows the correlation of asialo- with trisialo-transferring determined in % transferrin.

FIG. 9 shows the correlation of asialo- with trisialo-transferrin, determined in % transferrin. As expected, no correlation was found. The squared correlation coefficient was very low, at 0.01754. The graph is produced using data from the RIA method.

Figure 10:
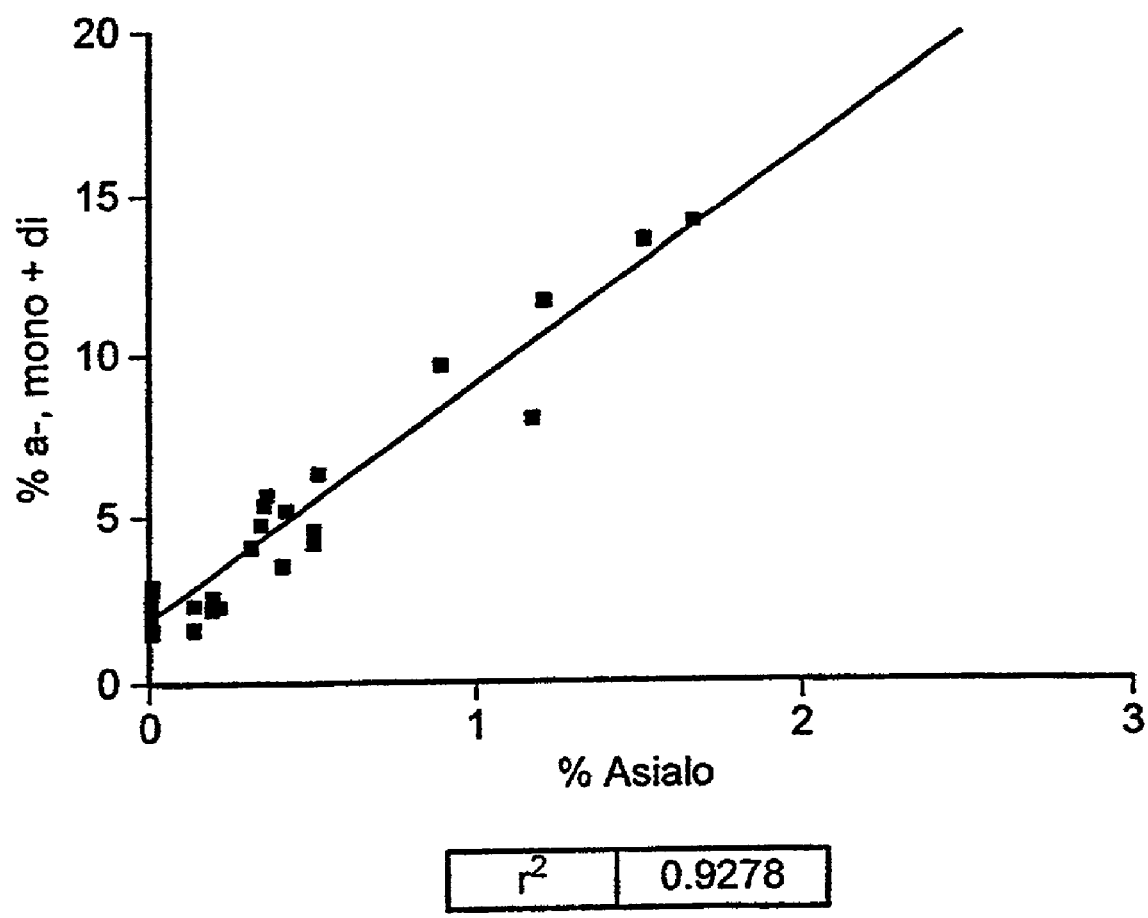
FIG. 10 shows the correlation of (asialo-, monosialo- and disialo-transferrin) with asialotransferrin, determined in % transferrin.

FIG. 10 shows the correlation of (asialo-, monosialo- and disialo-transferrin) with asialotransferrin, determined in % transferrin. The squared correlation coefficient was 0.9278. The graph is produced using data from the RIA method.

Figure 11:
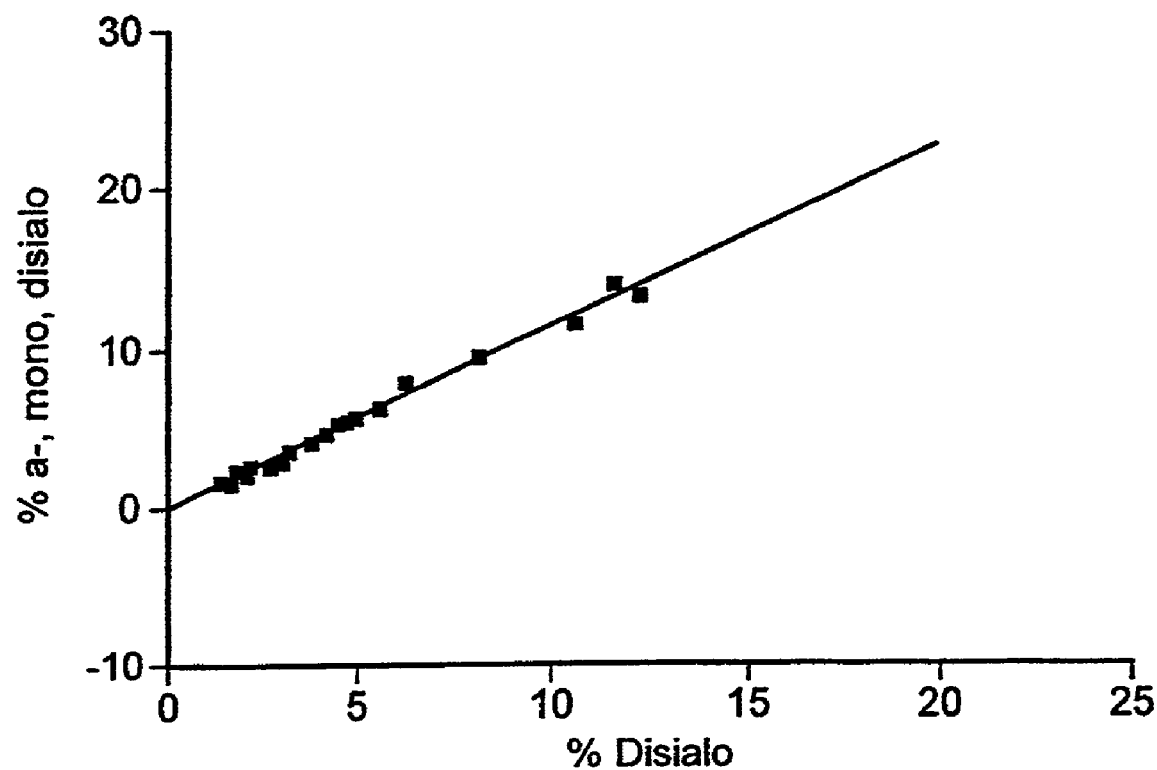
FIG. 11 shows the correlation of (asialo-, monosialo- and disialo-transferring with disialotransferrin, determined in % transferrin.

FIG. 11 shows the correlation of (asialo-, monosialo- and disialo-transferrin) with disialotransferrin, determined in % transferrin. The squared correlation coefficient was 0.9906. The graph is produced using data from the RIA method.

ferrin variants, which may be used as a diagnostic tool for alcohol consumption, in a sample of body fluid, said method comprising:

(a) obtaining at least two solutions, each having known contents of asialo- (A1, A2, A3, etc.) and disialo-transferrins (D1, D2, D3, etc.);

(b) subjecting each of said solutions to a separation method to separate fractions substantially free from tri- and higher sialylated transferrins;

(c) determining the total transferrin variant content (T1, T2, T3, etc.) of said fractions;

(d) determining the correlation between the content of asialo- and disialo-transferrins or between the content of asialo-, monosialo, and disialo-transferrins in the sample;

(e) producing a calibration curve based on the determined correlation between the content of asialo- and disialo-transferrins or the content of asialo-, monosialo, and disialo-transferrins in the sample;

(f) using the calibration curve to produce an algorithm that relates the content of asialo- and disialo-transferrins or the content of asialo-, monosialo, and disialo-transferrins in the sample to the content or amount of one or more transferrin variants in the sample; and (g) determining the content of a transferrin variant or combination of transferrin variants in the sample.

2. The method of claim 1 wherein the algorithm is capable of determining the content of a carbohydrate-deficient transferrin (CDT) variant or combination of CDT variants.

3. The method of claim 1 wherein said algorithm is capable of determining the content or amount of asialo- or disialo-transferrin.

4. The method of claim 1 wherein said algorithm is capable of determining the content or amount of asialo-, monosialo- and disialo-transferrins.

5. The method of claim 1 wherein said algorithm is based upon a quantitation of each of the isoforms of transferrin having zero, one or two sialic acid residues per molecule.

6. The method of claim 1 wherein said algorithm is produced on the basis of a correlation between the content of asialo- and disialo-transferrins in a sample.

7. The method of claim 1 wherein the algorithm is produced on the basis of a correlation between the content of asialo-, monosialo-, and disialo-transferrins in a sample.

8. The method of claim 1 wherein said algorithm is defined by at least one of the following equations:

$$A=(T-(db))/(c+(da))$$

$$D=b+a(T-(db))/(c+(da))$$

$$CDT=A+D=b+(a+1)(T-(db))/(c+(da))$$

wherein

T represents the determined total transferrin content in the determined fraction;

A represents the actual asialotransferrin content in the sample;

D represents the actual disialotransferrin content in the sample;

CDT represents the actual total content of asialo-, monosialo- and disialotransferrins in the sample;

a and b are constants defining the correlation between A and D in any serum sample; and c and d are constants specific to the determination step b).

9. A method for determining the content of a transferrin variant or combination of transferrin variants, which may be used as a diagnostic tool for alcohol consumption, in a sample of body fluid, said method comprising:

(a) obtaining at least two solutions, each having known contents of asialo- (A1, A2, A3, etc.) and disialo-transferrins (D1, D2, D3, etc.) , wherein the solutions are substantially free from tri- and higher sialylated transferrins;

(b) determining the total transferrin variant content (T1, T2, T3, etc.) of said solutions; and (c) determining the content of any transferrin variant or combination of transferrin variants in said sample of body fluid using an algorithm produced by the method of claim 1.

10. A method for determining the content of a transferrin variant or combination of transferrin variants, which may be used as a diagnostic tool for alcohol consumption, in a body fluid said method comprising:

(a) determining the content in a sample of body fluid of a first transferrin variant or a first combination of transferrin variants, wherein the first transferrin variant is asialotransferrin, monosialotransferrin, or disialotransferrin, and wherein the first combination of transferrin variants is asialotransferrin and monosialotransferrin, asialotransferrin and disialotransferrin, or monosialotransferrin and disialotransferrin, wherein the sample is substantially free from tri- and higher sialylated transferrins;

(b) determining the total transferrin variant content in said sample; and (c) determining the content of any a second transferrin variant or a second combination of transferrin variants, wherein the second transferrin variant is asialotransferrin, monosialotransferrin or disialotransferrin, and wherein the second combination of transferrin variants is asialotransferrin and monosialotransferrin, asialotransferrin and disialotransferrin, or monosialotransferrin and disialotransferrin; wherein the second transferrin variant is not the first transferrin variant and the second combination of transferrin variants is not the first combination of transferrin variants, or combination of transferrin variants in said sample wherein the determination (c) is made using an algorithm produced by a method comprising:

(i) obtaining at least two solutions, each having known contents of asialo-(A1, A2, A3, etc.) and disialo-transferrins (D1, D2, D3, etc.);

(ii) subjecting each of said solutions to a separation method to separate fractions substantially free from tri- and higher sialylated transferrins;

(iii) determining the total transferrin variant content (T1, T2, T3, etc.) of said fractions; and (iv) using an algorithm capable of determining the content of a transferrin variant or combination of transferrin variants in a given sample of body fluid subjected to said separation step (ii) wherein the algorithm is produced by the method of claim 1.

11. A method for determining the content of a transferrin variant or combination of transferrin variants, which may be used as a diagnostic tool for alcohol consumption, in a sample of body fluid said method comprising:

(a) subjecting the sample of body fluid to a separation method to generate a fraction of the sample substantially free from tri- and higher sialylated transferrins;

(b) determining the total transferrin variant content in said fraction; and (c) determining the content of any one of transferrin variant asialotransferrin, disialotransferrin, or the combination of asialotransferrin, monosialotransferrin and disialotransferrin transferrin variants in said sample, wherein the determination (c) is made using an algorithm produced by a method comprising:

(i) obtaining at least two solutions, each having known contents of asialo-(A1, A2, A3, etc.) and disialo-transferrins (D1, D2, D3, etc.);

(ii) subjecting each of said solutions to a separation method to separate fractions substantially free from hi- and higher sialylated transferrins;

(iii) determining the total transferrin variant content (T1, T2, T3, etc.) of said fractions;

(iv) determining the correlation between the content of asialo- and disialo-transferrins or between the content of asialo-, monosialo, and disialo-transferrins in the sample;

(v) producing a calibration curve based on the determined correlation between the content of asialo- and disialo-transferrins or the content of asialo-, monosialo, and disialo-transferrins in the sample; and (vi) using the calibration curve to produce an algorithm that relates the content of asialo- and disialo-transferrins or the content of asialo-, monosialo, and disialo-transferrins in the sample to the content or amount of one or more transferrin variants in the sample.

12. The method of claim 11 wherein the transferrin variant or combination of transferrin variants is a carbohydrate-deficient transferrin (CDT) variant or combination of CDT variants.

13. The method of claim 1 wherein said body fluid is blood or a blood-derived sample.

14. The method of claim 11 wherein said body fluid is blood or a blood-derived sample.

15. The method of claim 1 wherein each of the fractions substantially free from tri- and higher sialylated transferrins comprises at least 60% of the asialo- and monosialo-transferrin variants present in the sample prior to separation.

16. The method of claim 11 wherein the fraction substantially free from tri- and higher sialylated transferrins comprises at least 60% of the asialo- and monosialo-transferrin variants present in the sample prior to separation.

17. The method of claim 1 wherein each of the fractions substantially free from tri- and higher sialylated transferrins has a disialotransferrin content of at least 20% of the total disialotransferrin content of the sample prior to separation.

18. The method of claim 11 wherein the fraction substantially free from tri- and higher sialylated transferrins has a disialotransferrin content of at least 20% of the total disialotransferrin content of the sample prior to separation.

19. The method of claim 1 wherein each of the fractions substantially free from tri- and higher sialylated transferrins comprises less than 20% asialotransferrin, less than 5% monosialotransferrin and 70 to 80% disialotransferrin.

20. The method of claim 11 wherein the fraction substantially free from tri- and higher sialylated transferrins comprises less than 20% asialotransferrin, less than 5% monosialotransferrin and 70 to 80% disialotransferrin.

21. The method of claim wherein at least 70 to 80% of the transferrin molecules in each of the fractions substantially free from tri- and higher sialylated transferrins carry a carbohydrate chain or a residue thereof.

22. The method of claim 11 wherein at least 70 to 80% of the transferrin molecules in the fraction substantially free from tri- and higher sialylated transferrins carry a carbohydrate chain or a residue thereof.

23. The method of claim 1 wherein said separation method comprises the steps of contacting a sample of body fluid with a carbohydrate-binding ligand, followed by separation of a fraction not binding to said ligand.

24. The method of claim 23 wherein the carbohydrate-binding ligand is a lectin or a mixture of lectins.

25. The method of claim 11 wherein said separation method comprises the steps of contacting a sample of body fluid with a carbohydrate-binding ligand, followed by separation of a fraction not binding to said ligand.

26. The method of claim 25 wherein the carbohydrate-binding ligand is a lectin or a mixture of lectins.

27. The method of claim 24 wherein said carbohydrate-binding ligand is a sialic acid binding lectin.

28. The method of claim 26 wherein said carbohydrate-binding ligand is a sialic acid binding lectin.

29. A kit for a diagnostic assay for the assessment of alcohol consumption, said kit comprising:
at least two transferrin solutions having known asialo- and disialotransferrin concentrations;
means for subjecting a sample of body fluid to a determination step capable of determining the content of target asialotransferrin, monotransferrin and disialotransferrin, wherein the sample is substantially free from tri- and higher sialylated transferrins;
means for the detection of transferrin; and
means for determining the content of any asialo-, disialo-, trisialo-, tetra-, penta- or hexasialotransferrin variant or combination of asialo-, disialo-, trisialo-, tetra-, penta- or hexasialotransferrin variants in a sample of body fluid subjected to said determination step.

30. A kit for a diagnostic assay for the assessment of alcohol consumption, said kit comprising:
at least two transferrin solutions having known asialo- and disialotransferrin concentrations;
means for subjecting a sample of body fluid to a separation step capable of producing a fraction substantially free from tri-and higher sialylated transferrins;
means for the detection of transferrin; and
means for determining the content of any asialo-, disialo-, trisialo-, tetra-, penta- or hexasialotransferrin variant or combination of asialo-, disialo-, trisialo-, tetra-, penta- or hexasialotransferrin variants in a sample of body fluid subjected to said determination step.

31. The method of claim 9 wherein the transferrin variant or combination of transferrin variants is a carbohydrate-deficient transferrin (CDT) or a combination of CDT variants.

32. The method of claim 17 wherein each of the fractions substantially free from tri- and higher sialylated transferrins has a disialotransferrin content of up to 60 to 70% of the total disialotransferrin content of the sample prior to separation.

33. The method of claim 18 wherein the fraction substantially free from tri- and higher sialylated transferrins has a disialotransferrin content of up to 60 to 70% of the total disialotransferrin content of the sample prior to separation.

34. A method of producing an algorithm for determining the content of a transferrin variant or combination of transferrin variants, which may be used for diagnosing or monitoring of alcoholism, in a sample of body fluid, said method comprising:
(a) obtaining at least two solutions, each having known contents of asialo- (A1, A2, A3, etc.) and disialotransferrins (D1, D2, D3, etc.);
(b) subjecting each of said solutions to a separation method to separate fractions substantially free from tri- and higher sialylated transferrins;
(c) determining the total transferrin variant content (T1, T2, T3, etc.) of said fractions;
(d) determining the correlation between the content of asialo- and disialo-transferrins or between the content of asialo-, monosialo, and disialo-transferrins in the sample;
(e) producing a calibration curve based on the determined correlation between the content of asialo- and disialo-transferrins or the content of asialo-, monosialo, and disialo-transferrins in the sample; and
(f) using the calibration curve to produce an algorithm that relates the content of asialo- and disialo-transferrins or the content of asialo-, monosialo, and disialo-transferrins in the sample to the content or amount of one or more transferrin variants in the sample; and
(g) determining the content of a transferrin variant or combination of transferrin variants in the sample, which may be used for diagnosing or monitoring of alcoholism.

* * * * *